(12) United States Patent
Shcherbakova et al.

(10) Patent No.: US 7,491,728 B2
(45) Date of Patent: Feb. 17, 2009

(54) PYRIMIDINONE COMPOUNDS AS CALCILYTICS

(75) Inventors: Irina V. Shcherbakova, Salt Lake City, UT (US); Manuel F. Balanddrin, Salt Lake City, UT (US); Guangfei Huang, Alchua, FL (US); Otto Geoffroy, Alchua, FL (US); John Fox, Salt Lake City, UT (US); Robert Marquis, King of Prussia, PA (US); Dennis Shinji Yamashita, King of Prussia, PA (US); Juan Luengo, King of Prussia, PA (US); Wenyong Wang, King of Prussia, PA (US)

(73) Assignee: SmithKline Beecham Corp., Philadelphia, PA (US)

( * ) Notice: Subject to any disclaimer, the term of this patent is extended or adjusted under 35 U.S.C. 154(b) by 0 days.

(21) Appl. No.: 10/552,363

(22) PCT Filed: Apr. 7, 2004

(86) PCT No.: PCT/US2004/010638

§ 371 (c)(1),
(2), (4) Date: Nov. 20, 2006

(87) PCT Pub. No.: WO2004/092120

PCT Pub. Date: Oct. 28, 2004

(65) Prior Publication Data

US 2007/0197555 A1   Aug. 23, 2007

(51) Int. Cl.
*A61K 31/517* (2006.01)
*A61K 31/50* (2006.01)
*C07D 403/14* (2006.01)
*C07D 239/30* (2006.01)
*C07D 239/46* (2006.01)
*A61P 35/00* (2006.01)

(52) U.S. Cl. ............... 514/266.21; 514/269; 514/258.1; 514/266.31; 544/284; 544/289; 544/298; 544/253

(58) Field of Classification Search ............. 514/266.1, 514/266.21, 269, 258.1, 266.31; 544/284, 544/289, 253, 298
See application file for complete search history.

(56) References Cited

U.S. PATENT DOCUMENTS

| | | | | |
|---|---|---|---|---|
| 3,185,689 A | * | 5/1965 | Ruschg et al. | ............... 544/319 |
| 5,300,477 A | * | 4/1994 | Tice | ............... 504/242 |
| 5,726,124 A | * | 3/1998 | Tice et al. | ............... 504/193 |
| 5,948,775 A | | 9/1999 | Koko et al. | |

FOREIGN PATENT DOCUMENTS

WO   WO 2004/092121 A2   10/2004

OTHER PUBLICATIONS

Nemeth, J. Molec. Endocrin., 2002, 29, 15-21.*
Fox, Current Opinion in Pharm, 2002, 2: 338-344.*

(Continued)

*Primary Examiner*—Mark L Berch
*Assistant Examiner*—Cecilia M Jaisle
(74) *Attorney, Agent, or Firm*—Mary E. McCarthy; Stephen Venetianer; Charles M. Kinzig

(57) ABSTRACT

The pyrimidinone compounds are disclosed. Methods of preparing the pyrimidinone compounds are also disclosed.

16 Claims, 1 Drawing Sheet

Effect of bolus i.v. injection of compound of Example 9 on plasma PTH levels in normal rats

OTHER PUBLICATIONS

Nemeth, Cell Calcium, 35 (2004) 283-289.*
Stewart, N. Eng. J. Med. 351: 4, Jul. 2004, 324-326.*
Cunningham, J. Am. Soc. Nephrol. 18: 223-234, 2007.*
Stajer, et al., Magyar Kemiai Folyoirat (1986), 92(5), 234-6 (Abstract).*
Fulop, et al., Synthesis (1985), (12), 1148-9.*
Schubert, et al., Journal fuer Praktische Chemie (Leipzig) (1970), 312(3), 494-506.*
Sprio, et al., Ann. di Chim. (Rome, IT) (1970), 60(5), 393-6.*
Kato, et al., Yakugaku Zasshi (1970), 90(4), 509-11.*
Mitter, et al., Quart. J. Indian Chem. Soc. (1927), 4, 149-57.*
Mitter, et al., Quart. J. Indian Chem. Soc. (1925), 2, 61-70.*
Mitter, et al., Journal of the Chemical Society, Transactions (1923), 123, 2179-84.*
Arai, et al., Heterocycles (2001), 55(12), 2283-2287.*
Tice, et al., Tetrahedron (2001), 57(14), 2689-2700.*
Jayakumar, et al., Tetrahedron Letters (2001), 42(11), 2235-2237.*
Rossi, et al., Tetrahedron (1999), 55(22), 6921-6970.*
Mukherjee, et al., Heterocycles (1998), 47(2), 933-950.*
Rossi, et al., Tetrahedron (1997), 53(41), 14107-14114.*
Holzer, et al., Liebigs Annalen der Chemie (1994), (9), 901-9.*
Mazumdar, et al., Tetrahedron (1994), 50(25), 7579-88.*
Gupta, et al., India Patent 158084, issued Aug. 30, 1986.*
Jeong, An Efficient Synthesis of 3-Substituted 3$H$-Pyrimidin-4ones, Organic Letters, vol. 6, No. 6, 2004 (pp. 1013-1016).
Juby, Peter F., et al: "Antiallergy agents. 2. 2-Phenyl-5-(1H-tetrazol-5-yl) pyrimidin-4(3H)-ones" Journal of Medicinal Chemistry (1982) 25(10), 1145-50.
Database Caplus [Online], Chemical Abstracts Service, Columbus, Ohio, US; Krivopalov, V.P. et al: ynthesis of 2- and 4-chloroprimides bearing hydroxyphenyl substituents by reaction of Vilsmeier-Haack reagents with (hydroxyphenyl)pyrimidin-2- and -4-ones XP002484028 1993.
Database Caplus [Online], Chemical Abstracts Service, Columbus Ohio, US; Krivopalov, V.P., et al: "Method of preparing chloro azines containing an o-hydroxyphenyl group" XP002484029 1995.
Database Caplus [Online] Chemical Abstracts Service, Columbus, Ohio, US; Miyazaki, Hiroshi, et al: "2-Substituted-4-methyl-6-pyrimidone" XP002484027 1973.

* cited by examiner

US 7,491,728 B2

PYRIMIDINONE COMPOUNDS AS CALCILYTICS

TECHNICAL FIELD

The present invention relates to substituted 3H-pyrimidin-4-ones able to inhibit calcium receptor activity, methods for preparing and the uses of such compounds. Preferably, the compounds described herein are administered to patients to achieve a therapeutic effect.

BACKGROUND OF THE INVENTION

The present invention relates to novel calcilytic compounds, methods for preparing these compounds, pharmaceutical compositions containing these compounds, pharmaceutical compositions containing these compounds and their uses as calcium receptor antagonists.

In mammals, extracellular Ca2+ is under rigid homeostatic control and regulates various processes such as blood clotting, nerve and muscle excitability, and proper bone formation. Extracellular Ca2+ inhibits the secretion of parathyroid hormone ("PTH") from parathyroid cells, inhibits bone resorption by osteoclasts, and stimulates secretion of calcitonin from C-cells. Calcium receptor proteins enable certain specialized cells to respond to changes in extracellular Ca2+ concentration.

PTH is the principal endocrine factor regulating Ca2+ homeostasis in the blood and extracellular fluids. PTH, by acting on bone and kidney cells, increases the level of Ca2+ in the blood. This increase in extracellular Ca2+ then acts as a negative feedback signal, depressing PTH secretion. The reciprocal relationship between extracellular Ca2+ and PTH secretion forms an important mechanism maintaining bodily Ca2+ homeostasis.

Extracellular Ca2+ acts directly on parathyroid cells to regulate PTH secretion. The existence of a parathyroid cell surface protein which detects changes in extracellular $Ca^{2+}$ has been confirmed [see Brown et al., Nature, 366, 574, (1993)]. In parathyroid cells, this protein, the calcium receptor, acts as a receptor for extracellular $Ca^{2+}$, detects changes in the ion concentration of extracellular Ca2+, and initiates a functional cellular response, PTH secretion.

Extracellular Ca2+ influences various cell functions, reviewed in Nemeth et al., Cell Calcium, 11, 319 (1990). For example, extracellular Ca2+ plays a role in parafollicular (C-cells) and parathyroid cells [see Nemeth, Cell Calcium, 11, 323 (1990)]. The role of extracellular Ca2+ on bone osteoclasts has also been studied [see Zaidi, Bioscience Reports, 10, 493 (1990)].

Various compounds are known to mimic the effects of extra-cellular $Ca^{2+}$ on a calcium receptor molecule. Calcilytics are compounds able to inhibit calcium receptor activity, thereby causing a decrease in one or more calcium receptor activities evoked by extracellular $Ca^{2+}$. Calcilytics are useful as lead molecules in the discovery, development, design, modification and/or construction of useful calcium modulators, which are active at $Ca^{2+}$ receptors. Such calcilytics are useful in the treatment of various disease states characterized by abnormal levels of one or more components, e.g., polypeptides such as hormones, enzymes or growth factors, the expression and/or secretion of which is regulated or affected by activity at one or more $Ca^{2+}$ receptors. Target diseases or disorders for calcilytic compounds include diseases involving abnormal bone and mineral homeostasis.

Abnormal calcium homeostasis is characterized by one or more of the following activities: an abnormal increase or decrease in serum calcium; an abnormal increase or decrease in urinary excretion of calcium; an abnormal increase or decrease in bone calcium levels (for example, as assessed by bone mineral density measurements); an abnormal absorption of dietary calcium; an abnormal increase or decrease in the production and/or release of messengers which affect serum calcium levels such as PTH and calcitonin; and an abnormal change in the response elicited by messengers which affect serum calcium levels.

Thus, calcium receptor antagonists offer a unique approach towards the pharmacotherapy of diseases associated with abnormal bone or mineral homeostasis, such as hypoparathyroidism, osteosarcoma, periodontal disease, fracture healing, osteoarthritis, rheumatoid arthritis, Paget's disease, humoral hypercalcemia associated with malignancy and fracture healing, and osteoporosis.

DETAILED DESCRIPTION OF PREFERRED EMBODIMENTS

Figure 1:
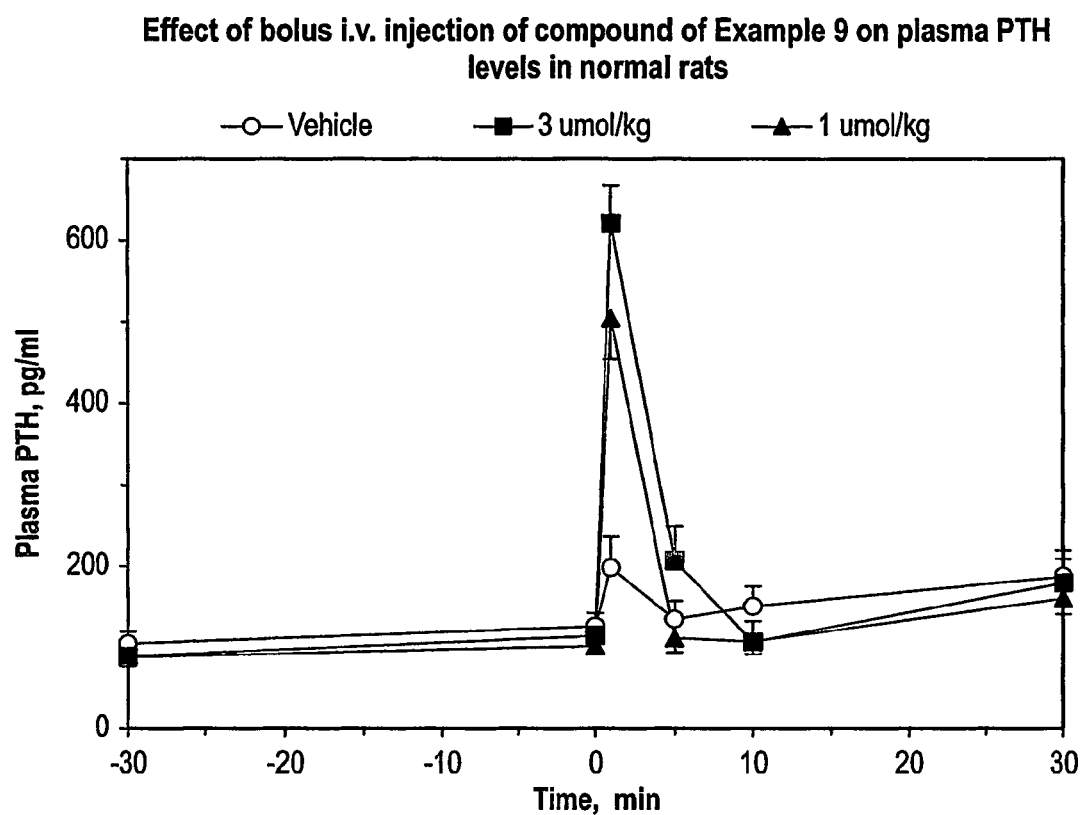
FIG. 1 is a graph which depicts the effect of bolus i.v. injection of the compound of Example 9 on plasma PTH levels in normal rats.

The present invention features calcilytic compounds. "Calcilytic compounds" refer to compounds able to inhibit calcium receptor activity. The ability of a compound to "inhibit calcium receptor activity" means that the compound causes a decrease in one or more calcium receptor activities evoked by extracellular $Ca^{2+}$.

The use of calcilytic compounds to inhibit calcium receptor activity and/or achieve a beneficial effect in a patient are described below. More specifically, the present application demonstrates the ability of calcilytic compounds to increase PTH secretion, thereby confirming that the parathyroid gland calcium receptor is a target site for these compounds. Also described below are techniques which can be used to obtain additional calcilytic compounds.

Examples of the featured calcilytic compounds representing 2,3,5,6-substituted 3H-pyrimidin-4-ones are provided by the chemical formula depicted in Structure I and the accompanying description.

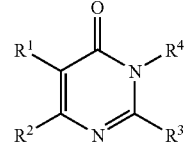

Structure I wherein:
$R^1$ and $R^2$ are independently one of: H, halogen, CN, $CF_3$, lower alkyl, cycloalk, and aryl; or $R^1$ and $R^2$ are together —$(CH_2)_n$— and n is 5, 4, or 3;
$R^3$ is an aryl group, which may have 1 to 4 substituents in the aryl ring and each substituent is one of: H, halogen, CN, $CF_3$, $OCF_3$, lower alkyl, N(lower alkyl)$_2$, lower alkoxy, OH, OC(O)-lower alkyl, OC(O)-lower alkylamino, and OC(O)-lower alkyl-N(lower alkyl)$_2$;
$R^4$ is one of H, lower alkyl, and a group of the formula —$(CH_2)_n$—$R^5$ wherein n is 0, 1, or 2, and $R^5$ is an aryl group which may have 1 to 3 substituents on the aryl ring and each substituent is one of: H, halogen, CN, $CF_3$, OCF₃, lower alkyl, lower alkoxy, NH-lower alkyl, NH-alkylaryl, N(lower alkyl)₂, OH, OC(O)-lower alk, OC(O)-lower alkylamino, and OC(O)-lower alkyl-N(lower alk)₂; and pharmaceutically acceptable salts and complexes thereof.

In embodiments wherein $R^1$ and $R^2$ are independently selected, $R^1$ and $R^2$ may be one of: lower alkyl, cycloalkyl and aryl or one of lower alkyl and cycloalkyl. In embodiments wherein $R^1$ and $R^2$ are together —(CH₂)$_n$—, n may be 4 or 3.

In embodiments wherein $R^3$ is a phenyl group, the phenyl ring may have 1 to 3 substituents which are one of: H, halogen, lower alkyl, lower alkoxy and OH. Also, in other embodiments wherein $R^3$ is a phenyl group, the phenyl ring may have 1 to 3 substituents which are one of: H, halogen and OH.

In embodiments wherein $R^4$ is a group of the formula —(CH₂)$_n$—$R^5$, n is 1 or 2, and $R^5$ is an aryl group, 1 to 3 substituents on the aryl ring are one of: H, halogen, lower alkyl or lower alkoxy. Also, in embodiments wherein $R^4$ is a group of the formula —(CH₂)$_n$—$R^5$, n is 2, and $R^5$ is an aryl group, 1 to 3 substituents on the aryl ring are one of: H, halogen, lower alkyl and lower alkoxy.

"Alk" refers to either alkyl or alkenyl. "Lower alk" refers to either lower alkyl or lower alkenyl, preferably lower alkyl.

"Alkenyl" refers to an optionally substituted hydrocarbon group containing at least one carbon-carbon double bond between the carbon atoms and containing 2-6 carbon atoms joined together. The alkenyl hydrocarbon group may be straight-chain. Straight-chain alkenyl preferably has 2 to 4 carbons.

"Alkyl" refers to an optionally substituted hydrocarbon group joined by single carbon-carbon bonds and having 1 to 6 carbon atoms joined together. The alkyl hydrocarbon group may be straight-chain or contain one or more branches. In some embodiments, branched- and straight-chain alkyl groups have 1 to 4 carbons, each of which may be optionally substituted. Alkyl substituents are independently one of: lower alkyl, unsubstituted aryl, OH, NH₂, NH-lower alkyl, and N(lower alkyl)₂. In some embodiments, no more than two substituents are present. For example, alkyl may be a lower alkyl which is unsubstituted branched- or straight-chain alkyl having 1 to 4 carbons.

"Cycloalk" refers to an optionally substituted cyclic alkyl or an optionally substituted non-aromatic cyclic alkenyl and includes monocyclic and multiple ring structures such as bicyclic and tricyclic. The cycloalkyl has 3 to 15 carbon atoms. In one embodiment, cycloalkyl has 3 to 5 carbon atoms. Optional substituents for cycloalk are independently selected from the group described above for alkenyl. In one embodiment, no more than three substituents are present. In another embodiment, the cycloalk is unsubstituted. For example, the cylcoalk may be unsubstituted cyclic alkyl. Examples of suitable cycloalkyl groups include cyclopropyl and cyclobutyl.

"Aryl" refers to an optionally substituted aromatic group with at least one ring having a conjugated or fused ring system. Aryl includes carbocyclic aryl, heterocyclic aryl and biaryl groups, all of which may be optionally substituted. The aryl may be either optionally substituted phenyl or optionally substituted pyridyl.

"Alkoxy" refers to oxygen joined to an unsubstituted alkyl 1 to 4 carbon atoms in length. In one embodiment, the oxygen is joined to an unsubstituted alklyl 1 to 2 carbons in length. For example, the alkoxy may be methoxy.

Compounds which are particularly useful embodiments include:
5-ethyl-3-[2-(2-fluoro-phenylyethyl]-2-(2-hydroxy-phenyl)-6-methyl-3H-pyrimidin-4-one and
3-[2-(3-fluoro-phenyl)-ethyl]-2-(2-hydroxy-phenyl)-6-methyl-5-isopropyl-3H-pyrimidin-4-one.

An expanded list of compounds which are particularly useful embodiments include:
2-(2-hydroxy-phenyl)-5,6-dimethyl-3-phenethyl-3H-pyrimidin-4-one;
3-[2-(2-fluoro-phenyl)-ethyl]-2-(2-hydroxy-phenyl)-5,6-dimethyl-3H-pyrimidin-4-one;
3-[2-(3-fluoro-phenyl)-ethyl]-2-(2-hydroxy-phenyl)-5,6-dimethyl-3H-pyrimidin-4-one;
3-[2-(4-fluoro-phenyl)-ethyl]-2-(2-hydroxy-phenyl)-5,6-dimethyl-3H-pyrimidin-4-one;
5-ethyl-2-(2-hydroxy-phenyl)-6-methyl-3-phenethyl-3H-pyrimidinone;
5-ethyl-3-[2-(2-fluoro-phenyl)-ethyl]-2-(2-hydroxy-phenyl)-6-methyl-3H-pyrimidin-4-one;
5-ethyl-3-[2-(3-fluoro-phenylyethyl]-2-(2-hydroxy-phenyl)-6-methyl-3H-pyrimidin-4-one;
5-ethyl-3-[2-(4-fluoro-phenyl)-ethyl]-2-(2-hydroxy-phenyl)-6-methyl-3H-pyrimidin-4-one;
3-[2-(3-fluoro-phenyl)-ethyl]-2-(2-hydroxy-phenyl)-6-methyl-5-propyl-3H-pyrimidin-4-one;
3-[2-(3-fluoro-phenyl)-ethyl]-2-(2-hydroxy-phenyl)-5-isopropyl-6-methyl-3H-pyrimidin-4-one;
3-[2-(2-fluoro-phenyl)-ethyl]-2-(2-hydroxy-phenyl)-5-isopropyl-6-methyl-3H-pyrimidin-4-one;
2-(2-hydroxy-phenyl)-5-methyl-3-phenethyl-6-trifluoromethyl-3H-pyrimidin-4-one;
2-(2-hydroxy-phenyl)-3-phenethyl-5,6,7,8-tetrahydro-3H-quinazolin-4-one;
3-[2-(3-fluoro-phenyl)-ethyl]-2-(2-hydroxy-phenyl)-5,6,7,8-tetrahydro-3H-quinazolin-4-one;
5-cyclopropyl-3-[2-(3-fluoro-phenyl)-ethyl]-2-(2-hydroxy-phenyl)-6-methyl-3H-pyrimidin-4-one;
2-(2-hydroxy-phenyl)-3-phenethyl-3,5,6,7-tetrahydro-cyclopentapyrimidin-4-one;
3-[2-(3-fluoro-phenyl)-ethyl]-2-(2-hydroxy-phenyl)-3,5,6,7-tetrahydro-cyclopentapyrimidin-4-one;
5-ethyl-2-(3-fluoro-2-hydroxy-phenyl)-3-[2-(3-fluoro-phenyl)-ethyl]-6-methyl-3H-pyrimidin-4-one;
5-ethyl-2-(5-fluoro-2-hydroxy-phenyl)-3-[2-(3-fluoro-phenyl)-ethyl]-6-methyl-3H-pyrimidin-4-one; and
5-thyl-2-(2-fluoro-6-hydroxy-phenyl)-3-[2-(3-fluoro-phenyl)-ethyl]-6-methyl-3H-pyrimidin-4-one.

A more expanded list of compounds which are particularly useful embodiments include:
2-(2-hydroxy-phenyl)-6-methyl-3-phenethyl-3H-pyrimidin-4-one;
3-[2-(2-fluoro-phenyl)-ethyl]-2-(2-hydroxy-phenyl)-6-methyl-3H-pyrimidin-4-one;
3-[2-(3-fluoro-phenyl)-ethyl]-2-(2-hydroxy-phenyl)-6-methyl-3H-pyrimidin-4-one;
2-(2-hydroxy-phenyl)-5,6-dimethyl-3-phenethyl-3H-pyrimidin-4-one;
3-[2-(2-fluoro-phenyl)-ethyl]-2-(2-hydroxy-phenyl)-5,6-dimethyl-3H-pyrimidin-4-one;
3-[2-(3-fluoro-phenyl)-ethyl]-2-(2-hydroxy-phenyl)-5,6-dimethyl-3H-pyrimidin-4-one;
3-[2-(4-fluoro-phenyl)-ethyl]-2-(2-hydroxy-phenyl)-5,6-dimethyl-3H-pyrimidin-4-one;
5-ethyl-2-(2-hydroxy-phenyl)-6-methyl-3-phenethyl-3H-pyrimidin-4-one;

5-ethyl-3-[2-(2-fluoro-phenyl)-ethyl]-2-(2-hydroxy-phenyl)-6-methyl-3H-pyrimidin-4-one;
5-ethyl-3-[2-(3-fluoro-phenyl)-ethyl]-2-(2-hydroxy-phenyl)-6-methyl-3H-pyrimidin-4-one;
5-ethyl-3-[2-(4-fluoro-phenyl)-ethyl]-2-(2-hydroxy-phenyl)-6-methyl-3H-pyrimidin-4-one;
3-[2-(3-fluoro-phenyl)-ethyl]-2-(2-hydroxy-phenyl)-6-methyl-5-propyl-3H-pyrimidin-4-one;
3-[2-(3-fluoro-phenyl)-ethyl]-2-(2-hydroxy-phenyl)-5-isopropyl-6-methyl-3H-pyrimidin-4-one;
3-[2-(2-fluoro-phenyl)-ethyl]-2-(2-hydroxy-phenyl)-5-isopropyl-6-methyl-3H-pyrimidin-4-one;
2-(2-hydroxy-phenyl)-5-methyl-3-phenethyl-6-trifluoromethyl-3H-pyrimidin-4-one;
2-(2-hydroxy-phenyl)-3-phenethyl-5,6,7,8-tetrahydro-3H-quinazolin-4-one;
3-[2-(3-fluoro-phenyl)-ethyl]-2-(2-hydroxy-phenyl)-5,6,7,8-tetrahydro-3H-quinazolin-4-one;
5-cyclopropyl-3-[2-(3-fluoro-phenyl)-ethyl]-2-(2-hydroxy-phenyl)-6-methyl-3H-pyrimidin-4-one;
2-(2-hydroxy-phenyl)-3-phenethyl-3,5,6,7-tetrahydro-cyclopentapyrimidin-4-one;
3-[2-(3-fluoro-phenyl)-ethyl]-2-(2-hydroxy-phenyl)-3,5,6,7-tetrahydro-cyclopentapyrimidin-4-one;
5-ethyl-2-(3-fluoro-2-hydroxy-phenyl)-3-[2-(3-fluoro-phenyl)ethyl]-6-methyl-3H-pyrimidin-4-one;
5-ethyl-2-(5-fluoro-2-hydroxy-phenyl)-3-[2-(3-fluoro-phenyl)-ethyl]-6-methyl-3H-pyrimidin-4-one;
5-ethyl-2-(2-fluoro-6-hydroxy-phenyl)-3-[2-(3-fluoro-phenyl)-ethyl]-6-methyl-3H-pyrimidin-4-one;
2-(4-chloro-2-hydroxy-phenyl)-5-ethyl-3-[2-(3-fluoro-phenyl)ethyl]-6-methyl-3H-pyrimidin-4-one.
A further expanded list of useful compounds include:
2-(2-hydroxy-phenyl)-6-methyl-3-phenethyl-3H-pyrimidin-4-one;
3-[2-(2-fluoro-phenyl)-ethyl]-2-(2-hydroxy-phenyl)-6-methyl-3H-pyrimidin-4-one;
3-[2-(3-fluoro-phenyl)-ethyl]-2-(2-hydroxy-phenyl)-6-methyl-3H-pyrimidin-4-one;
2-(2-hydroxy-phenyl)-5,6-dimethyl-3-phenethyl-3H-pyrimidin-4-one;
3-[2-(2-fluoro-phenyl)-ethyl]-2-(2-hydroxy-phenyl)-5,6-dimethyl-3H-pyrimidin-4-one;
3-[2-(3-fluoro-phenyl)-ethyl]-2-(2-hydroxy-phenyl)-5,6-dimethyl-3H-pyrimidin-4-one;
3-[2-(4-fluoro-phenyl)-ethyl]-2-(2-hydroxy-phenyl)-5,6-dimethyl-3H-pyrimidin-4-one;
5-ethyl-2-(2-hydroxy-phenyl)-6-methyl-3-phenethyl-3H-pyrimidin-4-one;
5-ethyl-3-[2-(2-fluoro-phenyl)-ethyl]-2-(2-hydroxy-phenyl)-6-methyl-3H-pyrimidin-4-one;
5-ethyl-3-[2-(3-fluoro-phenyl)-ethyl]-2-(2-hydroxy-phenyl)-6-methyl-3H-pyrimidin-4-one;
5-ethyl-3-[2-(4-fluoro-phenyl)-ethyl]-2-(2-hydroxy-phenyl)-6-methyl-3H-pyrimidin-4-one;
3-[2-(3-fluoro-phenyl)-ethyl]-2-(2-hydroxy-phenyl)-6-methyl-5-propyl-3H-pyrimidin-4-one;
3-[2-(3-fluoro-phenyl)-ethyl]-2-(2-hydroxy-phenyl)-5-isopropyl-6-methyl-3H-pyrimidin-4-one;
3-[2-(2-fluoro-phenyl)-ethyl]-2-(2-hydroxy-phenyl)-5-isopropyl-6-methyl-3H-pyrimidin-4-one;
2-(2-hydroxy-phenyl)-5-methyl-3-phenethyl-6-trifluoromethyl-3H-pyrimidin-4-one;
2-(2-hydroxy-phenyl)-3-phenethyl-5,6,7,8-tetrahydro-3H-quinazolin-4-one;
3-[2-(3-fluoro-phenyl)-ethyl]-2-(2-hydroxy-phenyl)-5,6,7,8-tetrahydro-3H-quinazolin-4-one;

5-cyclopropyl-3-[2-(3-fluoro-phenyl)-ethyl]-2-(2-hydroxy-phenyl)-6-methyl-3H-pyrimidin-4-one;
2-(2-hydroxy-phenyl)-3-phenethyl-3,5,6,7-tetrahydro-cyclopentapyrimidin-4-one;
3-[2-(3-fluoro-phenyl)-ethyl]-2-(2-hydroxy-phenyl)-3,5,6,7-tetrahydro-cyclopentapyrimidin-4-one;
5-ethyl-2-(2-methoxy-phenyl)-6-methyl-3-phenethyl-3H-pyrimidin-4-one;
2-(5-chloro-2-hydroxy-pyridin-3-yl)-5-ethyl-3-[2-(3-fluoro-phenyl)-ethyl]-6-methyl-3H-pyrimidin-4-one;
5-ethyl-2-(3-fluoro-2-hydroxy-phenyl)-3-[2-(3-fluoro-phenyl)-ethyl]-6-methyl-3H-pyrimidin-4-one;
5-ethyl-2-(5-fluoro-2-hydroxy-phenyl)-3-[2-(3-fluoro-phenyl)-ethyl]-6-methyl-3H-pyrimidin-4-one;
5-ethyl-2-(2-fluoro-6-hydroxy-phenyl)-3-[2-(3-fluoro-phenyl)-ethyl]-6-methyl-3H-pyrimidin-4-one;
2-(5-bromo-2-hydroxy-phenyl)-5-ethyl-3-[2-(3-fluoro-phenyl)-ethyl]-6-methyl-3H-pyrimidin-4-one;
5-ethyl-3-[2-(3-fluoro-phenyl)-ethyl]-2-(2-hydroxy-3-isopropyl-phenyl)-6-methyl-3H-pyrimidin-4-one;
2-(3,5-dibromo-2-hydroxy-phenyl)-5-ethyl-3-[2-(3-fluoro-phenyl)-ethyl]-6-methyl-3H-pyrimidin-4-one;
2-(4-chloro-2-hydroxy-phenyl)-5-ethyl-3-[2-(3-fluoro-phenyl)-ethyl]-6-methyl-3H-pyrimidin-4-one;
An even more expanded list of useful compounds include:
2-(2-hydroxy-phenyl)-6-methyl-3-phenethyl-3H-pyrimidin-4-one;
3-[2-(2-fluoro-phenyl)-ethyl]-2-(2-hydroxy-phenyl)-6-methyl-3H-pyrimidin-4-one;
3-[2-(3-fluoro-phenyl)-ethyl]-2-(2-hydroxy-phenyl)-6-methyl-3H-pyrimidin-4-one;
2-(2-hydroxy-phenyl)-5,6-dimethyl-3-phenethyl-3H-pyrimidin-4-one;
3-[2-(2-fluoro-phenyl)-ethyl]-2-(2-hydroxy-phenyl)-5,6-dimethyl-3H-pyrimidin-4-one;
3-[2-(3-fluoro-phenyl)-ethyl]-2-(2-hydroxy-phenyl)-5,6-dimethyl-3H-pyrimidin-4-one;
3-[2-(4-fluoro-phenyl)-ethyl]-2-(2-hydroxy-phenyl)-5,6-dimethyl-3H-pyrimidin-4-one;
5-ethyl-2-(2-hydroxy-phenyl)-6-methyl-3-phenethyl-3H-pyrimidin-4-one;
5-ethyl-3-[2-(2-fluoro-phenyl)-ethyl]-2-(2-hydroxy-phenyl)-6-methyl-3H-pyrimidin-4-one;
5-ethyl-3-[2-(3-fluoro-phenyl)-ethyl]-2-(2-hydroxy-phenyl)-6-methyl-3H-pyrimidin-4-one;
5-ethyl-3-[2-(4-fluoro-phenyl)-ethyl]-2-(2-hydroxy-phenyl)-6-methyl-3H-pyrimidin-4-one;
3-[2-(3-fluoro-phenyl)-ethyl]-2-(2-hydroxy-phenyl)-6-methyl-5-propyl-3H-pyrimidin-4-one;
3-[2-(3-fluoro-phenyl)-ethyl]-2-(2-hydroxy-phenyl)-5-isopropyl-6-methyl-3H-pyrimidin-4-one;
3-[2-(2-fluoro-phenyl)-ethyl]-2-(2-hydroxy-phenyl)-5-isopropyl-6-methyl-3H-pyrimidin-4-one;
2-(2-hydroxy-phenyl)-5-methyl-3-phenethyl-6-trifluoromethyl-3H-pyrimidin-4-one;
2-(2-hydroxy-phenyl)-3-phenethyl-5,6,7,8-tetrahydro-3H-quinazolin-4-one;
3-[2-(3-fluoro-phenyl)-ethyl]-2-(2-hydroxy-phenyl)-5,6,7,8-tetrahydro-3H-quinazolin-4-one;
5-cyclopropyl-3-[2-(3-fluoro-phenyl)-ethyl]-2-(2-hydroxy-phenyl)-6-methyl-3H-pyrimidin-4-one;
2-(2-hydroxy-phenyl)-3-phenethyl-3,5,6,7-tetrahydro-cyclopentapyrimidin-4-one;
3-[2-(3-fluoro-phenyl)-ethyl]-2-(2-hydroxy-phenyl)-3,5,6,7-tetrahydro-cyclopentapyrimidin-4-one;
5-ethyl-2-(2-methoxy-phenyl)-6-methyl-3-phenethyl-3H-pyrimidinone;

3-[2-(3-fluoro-phenyl)-ethyl]-5-isopropyl-2-(2-methoxy-phenyl)-6-methyl-3H-pyrimidin-4-one;
2-(5-chloro-2-hydroxy-pyridin-3-yl)-5-ethyl-3-[2-(3-fluoro-phenyl)-ethyl]-6-methyl-3H-pyrimidin-4-one;
5-ethyl-2-(3-fluoro-2-hydroxy-phenyl)-3-[2-(3-fluoro-phenyl)-ethyl]-6-methyl-3H-pyrimid4-none;
5-ethyl-2-(5-fluoro-2-hydroxy-phenyl)-3-[2-(3-fluoro-phenyl)-ethyl]-6-methyl-3H-pyrimidin-4-one;
5-ethyl-2-(2-fluoro-6-hydroxy-phenyl)-3-[2-(3-fluoro-phenyl)-ethyl]-6-methyl-3H-pyrimidin-4-one;
2-(5-chloro-2-hydroxy-phenyl)-5-ethyl-3-[2-(3-fluoro-phenyl)-ethyl]-6-methyl-3H-pyrimidin-4-one;
2-(5-bromo-2-hydroxy-phenyl)-5-ethyl-3-[2-(3-fluoro-phenyl)-ethyl]-6-methyl-3H-pyrimidin-4-one;
5-Ethyl-3-[2-(3-fluoro-phenyl)-ethyl]-2-(2-hydroxy-3-isopropyl-phenyl)-6-methyl-3H-pyrimidin-4-one;
2-(3,5-Dibromo-2-hydroxy-phenyl)-5-ethyl-3-[2-(3-fluoro-phenyl)-ethyl]-6-methyl-3H-pyrimidin-4-one;
5-ethyl-2-(3-chloro-2-hydroxy-phenyl)-3-[2-(3-fluoro-phenyl)-ethyl]-6-methyl-3H-pyrimidin-4-one;
5-ethyl-3-[2-(3-fluoro-phenyl)ethyl]-2-(2-hydroxy-3-methyl-phenyl)-6-methyl-3H-pyrimidin-4-one;
2-(4-chloro-2-hydroxy-phenyl)-5-ethyl-3-[2-(3-fluoro-phenyl)-ethyl]-6-methyl-3H-pyrimidin-4-one; and
5-ethyl-3-[2-(3-fluoro-phenyl)-ethyl]-2-(2-hydroxy-4-methoxy-phenyl)-6-methyl-3H-pyrimidin-4-one.

The calcilytic compounds of Structure I wherein $R^1$ is hydrogen can be prepared using standard techniques [for example, see Eason et al., *J. Chem. Soc.* 2991-3000 (1931); Gardner et al., *J. Org. Chem.* 59, 6245-6250 (1994), Tice et al., *Tetrahedron*, 57, 2689-2700 (2001)].

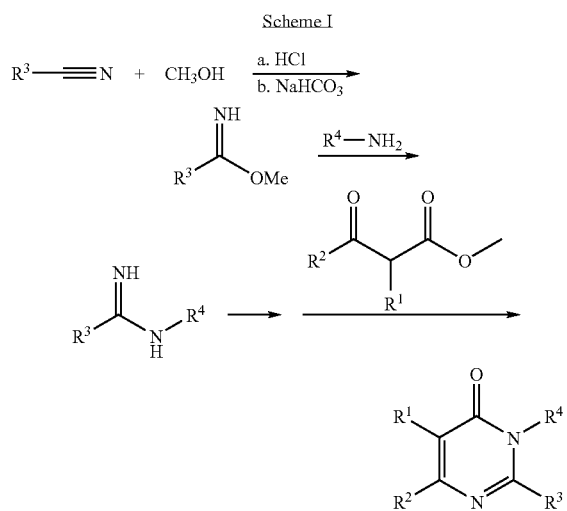

The calcilytic compounds of Structure I wherein $R^1$ and $R^2$ are substituents other than hydrogen can be prepared by Scheme II involving a method of cyclizing an appropriate acetic acid 2-(1-alkyl-2-$R^4$-carbamoyl-alk-1-enylcarbamoyl)-phenyl ester. A chemical synthesis for such compounds by Scheme II and by Method B in Example 13 is a novel approach to the synthesis of 2,3,5,6-substituted 3H-pyrimidin-4-ones which is an improvement in the art. This improvement is disclosed and claimed in co-pending U.S. patent application Ser. No. 10/551,920 titled Methods for Preparing 2,3,5,6-substituted 3H-pyrimidin-4-ones which was filed on Apr. 7, 2004 and is hereby incorporated by reference. Scheme II is provided below.

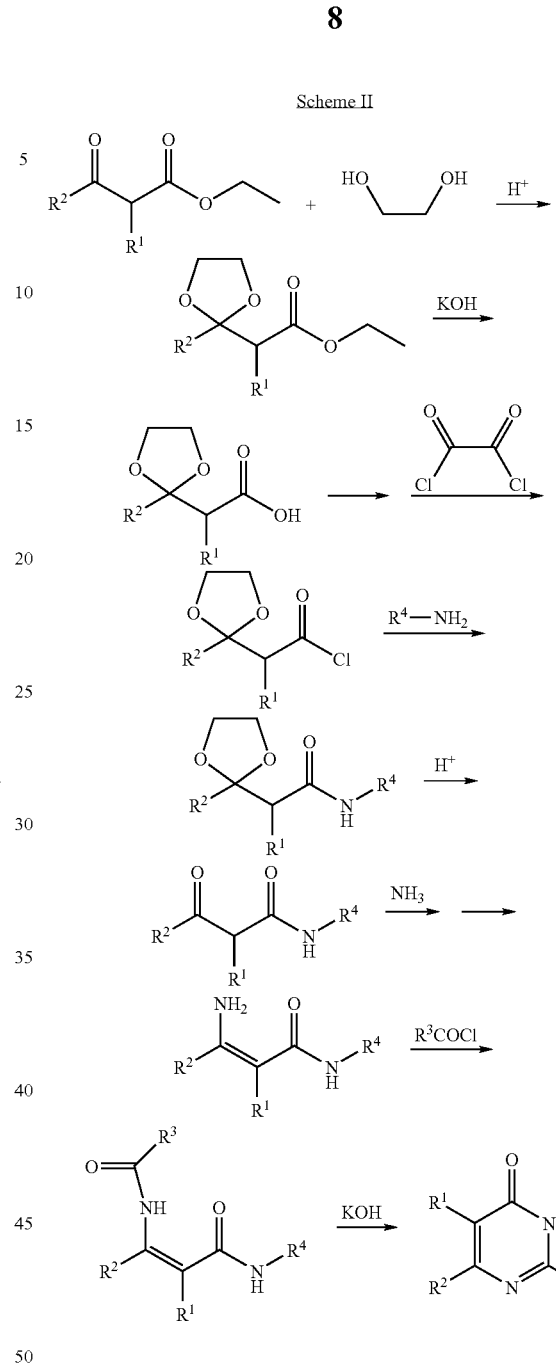

The chemical synthesis involves a method of making acetic acid 2-(1-alkyl-2—$R^4$-carbamoyl-alk-1-enylcarbamoyl)-phenyl esters of Structure II by standard techniques which includes acylation of an appropriate 3-amino-2-alkyl-alk-2-enoic acid $R^4$-amide of Structure III.

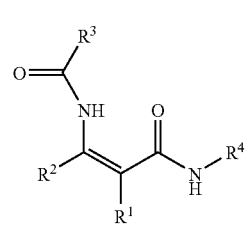

-continued

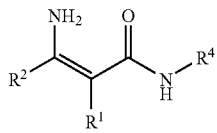

Structure III wherein:

$R^1$ and $R^2$ are independently one of: lower alkyl, cycloalk; or $R^1$ and $R^2$ are together —$(CH_2)_n$— and n is 5, 4, or 3;

$R^3$ is an aryl group, which may have 1 to 4 substituents in the aryl ring and each substituent is one of: H, halogen, lower alkyl, NH(lower alkyl), lower alkoxy, OH, OC(O)-lower alkyl, OC(O)-lower alkylamino, and OC(O)-lower alkyl-N(lower alkyl)$_2$;

$R^4$ is one of H, lower alkyl, or a group of the formula —$(CH_2)_n$—$R^5$ wherein n is 0, 1, or 2, $R^5$ is an aryl group which may have 1 to 3 substituents on the aryl ring and each substituent is one of: H, halogen, CN, $CF_3$, $OCF_3$, lower alkyl, lower alkoxy, NH-lower alkyl, NH-alkylaryl, N(lower alkyl)$_2$, OH, OC(O)-lower alk, OC(O)-lower alkylamino, and OC(O)-lower alkyl-N (lower alk)$_2$.

In embodiments wherein $R^1$ and $R^2$ are independently selected, $R^1$ and $R^2$ may be one of: lower alkyl and cycloalkyl. In embodiments wherein $R^1$ and $R^2$ are together —$(CH_2)_n$—, n may be 4 or 3.

In embodiments wherein $R^3$ is a phenyl group, the phenyl ring may have 1 to 3 substituents which are one of: H, halogen, lower alkyl, lower alkoxy and OH. Also, in other embodiments wherein $R^3$ is a phenyl group, the phenyl ring may have 1 to 3 substituents which are one of: H, halogen and OH.

In embodiments wherein $R^4$ is a group of the formula —$(CH_2)_n$—$R^5$, n is 1 or 2, and $R^5$ is an aryl group, 1 to 3 substituents on the aryl ring are one of: H, halogen, lower alkyl or lower alkoxy. Also, in embodiments wherein $R^4$ is a group of the formula —$(CH_2)_n$—$R^5$, n is 2, and $R^5$ is an aryl group, 1 to 3 substituents on the aryl ring are one of: H, halogen, lower alkyl and lower alkoxy.

In order to use a compound of Formula (I) or a pharmaceutically acceptable salt or complex thereof for the treatment of humans and other mammals, it is normally formulated in accordance with standard pharmaceutical practice as a pharmaceutical composition.

The calcilytic compounds can be administered by different routes including intravenous, intraperitoneal, subcutaneous, intramuscular, oral, topical (transdermal), or transmucosal administration. For systemic administration, oral administration is preferred. For oral administration, for example, the compounds can be formulated into conventional oral dosage forms such as capsules, tablets, and liquid preparations such as syrups, elixirs, and concentrated drops.

Alternatively, injection (parenteral administration) may be used, e.g., intramuscular, intravenous, intraperitoneal, and subcutaneous. For injection, the compounds of the invention are formulated in liquid solutions, preferably, in physiologically compatible buffers or solutions, such as saline solution, Hank's solution, or Ringer's solution. In addition, the compounds may be formulated in solid form and redissolved or suspended immediately prior to use. Lyophilized forms can also be produced.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays, rectal suppositories, or vaginal suppositories.

For topical administration, the compounds of the invention can be formulated into ointments, salves, gels, or creams, as is generally known in the art.

The amounts of various calcilytic compounds to be administered can be determined by standard procedures taking into account factors such as the compound $IC_{50}$, $EC_{50}$, the biological half-life of the compound, the age, size and weight of the patient, and the disease or disorder associated with the patient. The importance of these and other factors to be considered are known to those of ordinary skill in the art.

Amounts administered also depend on the routes of administration and the degree of oral bioavailability. For example, for compounds with low oral bioavailability, relatively higher doses may have to be administered.

Preferably the composition is in unit dosage form. For oral application, for example, a tablet or capsule may be administered, for nasal application, a metered aerosol dose may be administered, for transdermal application, a topical formulation or patch may be administered, and for transmucosal delivery, a buccal patch may be administered. In each case, dosing is such that the patient may administer a single dose.

Each dosage unit for oral administration contains suitably from 0.01 to 500 mg/Kg, and preferably from 0.1 to 50 mg/Kg, of a compound of Formula (I) or a pharmaceutically acceptable salt or complex thereof, calculated as the free base. The daily dosage for parenteral, nasal, oral inhalation, transmucosal or transdermal routes contains suitably from 0.01 mg to 100 mg/Kg, of a compound of Formula (I). A topical formulation contains suitably 0.01 to 5.0% of a compound of Formula (I). The active ingredient may be administered, for example, from 1 to 6 times per day, preferably once, sufficient to exhibit the desired activity, as is readily apparent to one skilled in the art.

As used herein, "treatment" of a disease includes, but is not limited to prevention, retardation and prophylaxis of the disease.

Diseases and disorders which might be treated or prevented, based upon the affected cells, include bone and mineral-related diseases or disorders; hypoparathyroidism; those of the central nervous system such as seizures, stroke, head trauma, spinal cord injury, hypoxia-induced nerve cell damage, such as occurs in cardiac arrest or neonatal distress, epilepsy, neurodegenerative diseases such as Alzheimer's disease, Huntington's disease and Parkinson's disease, dementia, muscle tension, depression, anxiety, panic disorder, obsessive-compulsive disorder, post-traumatic stress disorder, schizophrenia, neuroleptic malignant syndrome, and Tourette's syndrome; diseases involving excess water reabsorption by the kidney, such as syndrome of inappropriate ADH secretion (SIADH), cirrhosis, congestive heart failure, and nephrosis; hypertension; preventing and/or decreasing renal toxicity from cationic antibiotics (e.g., aminoglycoside antibiotics); gut motility disorders such as diarrhea and spastic colon; GI ulcer diseases; GI diseases with excessive calcium absorption such as sarcoidosis; autoimmune diseases and organ transplant rejection; squamous cell carcinoma; and pancreatitis.

In a preferred embodiment of the present invention, the present compounds are used to increase serum parathyroid hormone ("PTH") levels. Increasing serum PTH levels can be helpful in treating diseases such as hypoparathyroidism, osteosarcoma, periodontal disease, fracture, osteoarthritis, rheumatoid arthritis, Paget's disease, humoral hypercalcemia of malignancy, and osteoporosis.

In a preferred embodiment of the present invention, the present compounds are co-administered with an anti-resorptive agent. Such agents include, but are not limited to estrogen, 1,25-(OH)$_2$-vitamin D3, calcitonin, selective estrogen receptor modulators, vitronectin receptor antagonists, V—H+-ATPase inhibitors, src SH2 antagonists, bisphosphonates and cathepsin K inhibitors.

Another aspect of the present invention describes a method of treating a patient comprising administering to the patient an amount of a present compound sufficient to increase the serum PTH level. Preferably, the method is carried out by administering an amount of the compound effective to cause an increase in duration and/or quantity of serum PTH level sufficient to have a therapeutic effect.

In various embodiments, the compound administered to a patient causes an increase in serum PTH having a duration of up to one hour, about one to about twenty-four hours, about one to about twelve hours, about one to about six hours, about one to about five hours, about one to about four hours, about two to about five hours, about two to about four hours, or about three to about six hours.

In an alternative embodiment of the present invention, the compound administered to a patient causes an increase in serum PTH having a duration of more than about twenty-four hours provided that it is co-administered with an anti resorptive agent.

In additional different embodiments, the compound administered to a patient causes an increase in serum PTH of up to two-fold, two- to five-fold, five- to ten-fold, and at least 10-fold, greater than peak serum PTH in the patient. The peak serum level is measured with respect to a patient not undergoing treatment.

Composition of Formula (I) and their pharmaceutically acceptable salts and/or complexes, which are active when given orally, can be formulated as syrups, tablets, capsules, and lozenges. A syrup formulation will generally consist of a suspension or solution of the compound or salt in a liquid carrier such as, for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule, any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt or complex thereof which is active when administered in this way, with a binding and/or lubricating agent, for example polymeric glycols, gelatins, cocoa-butter or other low-melting vegetable waxes or fats or their synthetic analogs.

Typical dermal and transdermal formulations comprise a conventional aqueous or non-aqueous vehicle, for example a cream, ointment, lotion or pastep or are in the form of a medicated plaster, patch or membrane.

Preferably the composition is in unit dosage form, for example a tablet, capsule or metered aerosol dose, so that the patient may administer a single dose.

No unacceptable toxological effects are expected when compounds of the present invention are administered in accordance with the present invention.

EXAMPLES

The following specific examples are included for illustrative purposes only and are not to be considered as limiting to this disclosure. The reagents and intermediates used in the following examples are either commercially available or can be prepared according to standard literature procedures by those skilled in the art of organic synthesis.

HPLC (High Pressure Liquid Chromatography) analyses for 98+% purity confirmation were performed on a Shimadzu RID-10A Series HPLC equipped with a SPD-M10A VP diode array detector, two LC-AT pumps, and a SIL-10A autoinjector using either an Altima C18 (5μ, 4.6×259 mm) or an Intersil ODS2 (5μ, 4.6×59 mm) column.

NMR (Nuclear Magnetic Resonance) spectroscopy was performed on a Varian Gemini 300 spectrometer. Proton and carbon spectra were recorded at 300 MHz and 75 MHz, respectively, in deuterochloroform (CDCl$_3$), methanol-d$_4$ (CH$_3$OH-d$_4$), or dimethylsulfoxide-d$_6$ (DMSO-d$_6$) solutions. NMR resonances are reported in δ (ppm) relative to tetramethylsilane (TMS) as internal standard with the following descriptors for the observed multiplicities: s (singlet), d (doublet), t (triplet), q (quartet), dd (doublet of doublets), and m (multiplet). J$_{AB}$ coupling constants are reported in Hz.

Note that Examples 1-12 and 14-33 correspond with Examples 1-12 and 14-33 as presented in U.S. Provisional Application Ser. No. 60/479,323 which was filed on Jun. 18, 2003 and is titled Pyrimidinone Compounds as Calcilytics. Method A disclosed in Example 13 corresponds with Example 13 of Ser. No. 60/479,323. The examples also correspond with those as presented in U.S. Patent Application Ser. No. 60/460,859 which was filed on Apr. 7, 2003 and is titled Pyrimidinone Compounds as Calcilytics. In particular, Examples 1-12 correspond with Examples 1-12 in Ser. No. 60/460,859, Examples 15-17 correspond with Examples 14-16 in Ser. No. 60/460,859, and Examples 21-33 correspond with Examples 17-29 in Ser. No. 60/460,859. Method A disclosed in Example 13 corresponds with Example 13 of Ser. No. 60/460,859. Examples 4-20 correspond with Examples 1-17 in International Patent Application Serial No. 10/551,920, which is titled Methods for Preparing 2,3,5,6-substituted 3H-pyrimidin-4-ones and which was filed on Apr. 7, 2004. These applications are all incorporated herein by specific reference.

Example 1

Preparation of 2-(2-Hydroxy-phenyl)-6-methyl-3-phenethyl-3H-pyrimidin-4-one a.) 2-Hydroxy benzamidic acid methyl ester

Acetyl chloride (6.0 g, 76.4 mmol) was added drop-wise to methanol (10 mL) over 30 min. The temperature was kept at 20° C. by cooling the mixture in a water bath. After the addition of acetyl chloride, the solution was stirred for 2 h at room temperature. o-Hydroxybenzonitrile (4.0 g, 33.61 mmol) was added followed by toluene (20 mL). The mixture was stirred at room temperature under an argon atmosphere for 4 days. The precipitate was filtered and washed with toluene. After drying under high vacuum, 2-hydroxy-benzimidic acid methyl ester hydrochloride (2.2 g, 35%) was isolated as a white solid.

b.) 2-(2-Hydroxy-phenyl)-6-methyl-3-phenethyl-3H-pyrimidin-4-one

2-Hydroxy-benzimidic acid methyl ester from step 1a (250 mg, 1.33 mmol) was dissolved in methanol (6 mL) which contained sodium bicarbonate (110 mg, 1.33 mmol). After stirring at room temperature for 30 min, phenylethylamine (165 μl, 1.33 mmol) was added. The mixture was stirred for 4 h at room temperature, and then methyl acetoacetate (1.5 mL) and xylenes (10 mL) were added. Methanol was removed by distillation using a Dean-Stark trap, and the reaction mixture was refluxed for 3 h. The solution was cooled to room temperature and added to dichloromethane (100 mL). The mixture was extracted with water (100 mL) and the organic layer was dried with sodium sulfate containing decolorizing carbon. After filtration and concentration on the rotary evaporator, toluene (10 mL) was added to the residue, and the mixture was placed in the freezer overnight. The precipitate was filtered off and washed with cold toluene (5 mL). The product was further purified by flash chromatography on silica gel (25 g) with ethyl acetate—hexanes (7:3) as an eluent yielding 2-(2-hydroxy-phenyl)-6-methyl-3-phenethyl-3H-pyrimidin-4-one (120 mg, 22%) as a white solid.

$^1$H NMR (CDCl$_3$): δ 7.27-7.15 (m, 4H), 7.10 (dd, 1H, J=8.0, 1.5), 6.89-6.84 (m, 4H), 6.30 (s, 1H), 4.16 (t, 2H, J=7.5), 2.84 (t, 2H, J=7.5), 2.24 (s, 3H).

$^{13}$C NMR (CDCl$_3$): δ 162.97, 162.25, 159.06, 155.09, 137.70, 132.27, 129.09, 128.91, 128.83, 126.86, 120.19, 119.93, 117.68, 111.59, 47.81, 34.53, 23.37.

Example 2

Preparation of 3-[2-(2-Fluoro-phenyl)-ethyl]-2-(2-hydroxy-phenyl)-6-methyl-3H-pyrimidin-4-one Utilizing the methods described in Example 1 the title compound was prepared from 2-hydroxy-benzimidic acid methyl ester (750 mg, 4.0 mmol), 2-(2-fluoro-phenyl)-ethylamine (520 μl, 4.0 mmol) and methyl acetoacetate (4.0 mL) to provide 140 mg (10%) of 3-[2-(2-fluoro-phenyl)ethyl]-2-(2-hydroxy-phenyl)-6-methyl-3H-pyrimidin-4-one as a white solid after flash chromatography on ODS silica gel eluting with methanol-water (4:7) followed by recrystallization from a large volume of toluene (100 mL).

$^1$H NMR (CH$_3$OH-d$_4$): δ 7.38-7.29 (m, 1H), 7.20-7.17 (m, 1H), 7.01 (m, 6H), 6.37 (s, 1H), 4.13 (t, 2H, J=7.2), 2.92 (t, 2H, J=7.2), 2.28 (s, 3H).

$^{13}$C NMR(CH$_3$OH-d$_4$): δ 164.93, 164.48, 160.98, 155.53, 136.93, 133.05, 132.48, 130.77, 130.05, 129.94, 126.15, 125.93, 125.57, 123.07, 120.93, 118.18, 116.67, 116.33, 112.08, 47.16, 28.49, 23.21.

Example 3

Preparation of 3-[2-(3-Fluoro-phenyl)-ethyl]-2-(2-hydroxy-phenyl)-6-methyl-3H-pyrimidin-4-one Utilizing the methods described in Example 1 the title compound was prepared from 2-hydroxy-benzimidic acid methyl ester (500 mg, 2.67 mmol), 2-(3-fluoro-phenyl)-ethylamine (330 μl, 2.6 mmol) and methyl acetoacetate (3.0 mL) yielding 160 mg (10%) of 3-[2-(3-fluoro-phenyl)-ethyl]-2-(2-hydroxy-phenyl)-6-methyl-3H-pyrimidin-4-one as a white solid after two purifications by flash chromatography on ODS silica gel eluting with methanol-water (4.5:6.5) followed by recrystallization from a large volume of toluene (100 mL).

$^1$H NMR (DMSO-d$_6$): δ 10.20 (broad s, 1H), 7.36 (dd, 1H, J=7.5), 7.21 (m, 1H), 7.01-6.96 (m, 3H), 6.87 (dd, 1H, J=7.5), 6.60 (d, 1H, J=7.5), 6.52 (d, 1H, J=9.0), 6.30 (s, 1H), 3.93 (t, 2H, J=7.5), 2.75 (t, 2H, J=7.5), 2.19 (s, 3H).

$^{13}$C NMR (DMSO-d$_6$): δ 163.80, 162.65, 161.17, 158.17, 153.71, 140.84, 140.73, 131.21, 130.45, 130.34, 129.50, 124.53, 122.26, 119.07, 115.61, 115.26, 114.98, 113.48, 113.21, 110.45, 45.78, 33.29, 23.09.

Example 4

Preparation of 2-(2-Hydroxy-phenyl)-5,6-dimethyl-3-phenethyl-3H-pyrimidin-4-one a.) 2-(2-Methyl-[1,3]dioxolan-2-yl)-propionic acid ethyl ester

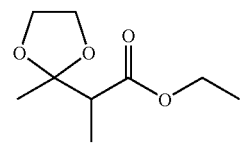

A mixture of 2-methyl-3-oxo-butyric acid ethyl ester (50 g, 0.347 mol), ethylene glycol (65 g, 1.05 mol) and p-toluenesulfonic acid monohydrate (0.2 g) in anhydrous toluene (200 mL) was refluxed using a Dean-Stark trap until the theoretical amount of water (6.3 mL) was collected. After cooling, the mixture was extracted with saturated bicarbonate solution (100 mL), water (100 mL×5), and brine (100 mL×2). After drying with sodium sulfate, filtration, and concentration on a rotary evaporator, the product was purified by distillation (fraction with b.p. 74-76° C./2 mm Hg) to yield 47.12 g (72%) of 2-(2-methyl-[1,3]dioxolan-2-yl)-propionic acid ethyl ester.

¹H NMR (CDCl₃): δ 4.16 (q, 2H, J=7.2), 3.97 (m, 4H), 2.76 (q, 1H, J=7.2), 1.41 (s, 3H), 1.27 (t, 3H, J=7.2), 1.23 (d, 3H, J=7.2).

¹³C NMR (CDCl₃): δ 173.24, 109.76, 64.81, 60.38, 47.88, 21.29, 14.14, 12.83.

b.) 2-(2-Methyl-[1,3]dioxolan-2-yl)-propionic acid

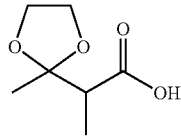

2-(2-Methyl-[1,3]dioxolan-2-yl)-propionic acid ethyl ester of Example 1a (31 g, 0.1647 mol) was dissolved in the mixture of dioxane-water (1:1, 350 mL) containing potassium hydroxide (35.63 g, 0.63 mol). The reaction mixture was stirred overnight at 35° C. and concentrated under high vacuum to give a white solid which was dissolved in water (200 mL) and extracted with dichloromethane (100 mL×2). The aqueous portion was acidified to pH=2 with 2N aqueous hydrochloric acid and the product was extracted with chloroform. The organic layer was washed with brine (300 mL), dried with sodium sulfate and concentrated under vacuum. 2-(2-methyl-[1,3]dioxolan-2-yl)-propionic acid was isolated as clear oil (20.34 g, 77%) which did not require further purification.

¹H NMR (CDCl₃): δ 11.29 (s, 1H), 4.01 (m, 4H), 2.80 (q, 1H, J=7.2), 1.43 (s, 3H), 1.26 (d, 3H, J=7.2).

¹³C NMR (CDCl₃): δ 178.61, 109.57, 64.84, 64.81, 47.80, 21.15, 12.61.

c.) 2-(2-Methyl-[1,3]dioxolan-2-yl)-N-phenethyl-propionamide 2-(2-Methyl-[1,3]dioxolan-2-yl)-propionic acid of Example 1b (1.60 g, 10 mmol) in dry dichloromethane (15 mL) was cooled to 0° C. under an argon atmosphere. A solution of oxalyl dichloride (2.92 g, 2.0 mL, 23.0 mmol) in dichloromethane (5 mL) was added dropwise. After 5 min at 0° C., the mixture was allowed to warm to room temperature. After stirring for 2 h at room temperature, the excess oxalyl dichloride was removed under reduced pressure to produce a yellow oil which was dissolved in dichloromethane (7 mL). The solution was cooled in an ice bath and phenethylamine (1.12 g, 10.0 mmol) in pyridine (5 mL) was added drop-wise. After the addition was complete, the reaction was warmed to room temperature and allowed to stir overnight. The solution was diluted with dicholoromethane (100 mL) and poured into ice-cold hydrochloric acid (1N, 150 mL). The organic layer was separated and washed with water (100 mL), sodium bicarbonate solution (5%, 50 mL), water (100 mL), and brine (100 mL). After drying with sodium sulfate and concentration on a rotary evaporator, the product was purified by flash chromatography on silica gel, eluting with hexanes-ethyl acetate (3:2) to give 2-(2-methyl-[1,3]dioxolan-2-yl)-N-phenethyl-propionamide (1.81 g, 69%) as colorless crystals.

¹H NMR (CDCl₃): δ 7.26 (m, 5H), 6.42 (broad s, 1H), 3.93 (m, 2H), 3.86 (m, 2H), 3.51 (m, 2H), 2.82 (t, 2H, J=7.2), 2.55 (q, 1H, J=7.2), 1.26 (s, 3H), 1.17 (d, 3H, J=7.2).

¹³C NMR (CDCl₃): δ 172.61, 138.99, 128.74, 128.43, 126.32, 109.77, 64.67, 64.50, 49.36, 40.45, 35.58, 21.20, 12.42.

d.) 2-Methyl-3-oxo-N-phenethyl-butyramide

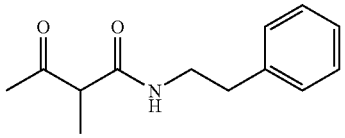

2-(2-Methyl-[1,3]dioxolan-2-yl)-N-phenethyl-propionamide of Example 1c (0.40 g, 1.5 mmol) was added to p-toluenesulfonic acid monohydrate (0.48 g, 2.5 mmol) in water (20 mmol) under a nitrogen atmosphere at room temperature. Acetone (20 mL) was added, and the reaction mixture was stirred overnight at room temperature and then heated at 95° C. for 3 h. After cooling to room temperature, the solution was made basic with sodium carbonate (0.5 g). The acetone was removed at room temperature under vacuum and the remaining aqueous material was extracted with dichloromethane (50 mL). The organic layer was washed with water (50 mL), brine (50 mL) and then dried with sodium sulfate. After concentration, the product was purified by crystallization from hexanes-ethyl acetate (1:1) to give 2-methyl-3-oxo-N-phenethyl-butyramide (0.17 g, 52%) as a white solid.

¹H NMR (CDCl₃): δ 7.26 (m, 5H), 6.13 (broad s, 1H), 3.52 (m, 2H), 3.34 (q, 1H, J=7.2), 2.81 (t, 2H, J=7.2), 2.19 (s, 3H), 1.34 (d, 3H, J=7.2).

¹³C NMR (CDCl₃): δ 207.27, 169.17, 138.54, 128.69, 128.61, 126.56, 54.98, 40.72, 35.55, 28.49, 14.58.

e.) 3-Amino-2-methyl-but-2-enoic acid phenethyl-amide

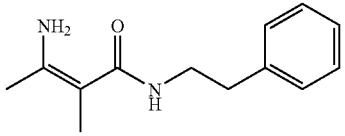

A solution of 2-methyl-3-oxo-N-phenethyl-butyramide of Example 1d (1.10 g, 5.00 mmol) in diethyl ether (300 mL) was saturated with gaseous ammonia for 3 h while cooled in an ice bath. Anhydrous aluminum chloride (99.99% purity, 0.667 g, 5.00 mmol) was then added in small portions and the reaction was allowed to stir at room temperature overnight. The reaction mixture was filtered and concentrated under reduced pressure to give 3-amino-2-methyl-but-2-enoic acid phenethyl-amide (0.97 g, 85% conversion by NMR) as a white solid which was used without purification for the next synthetic step.

f.) Acetic acid 2-(1-methyl-2-phenethylcarbamoyl-propenylcarbamoyl)-phenyl ester

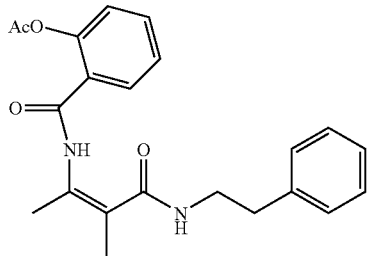

3-Amino-2-methyl-but-2-enoic acid phenethyl-amide of Example 1e (0.97 g, 5 mmol) was dissolved in tetrahydrofuran (20 mL) and pyridine (1.0 mL). Acetic acid 2-chlorocarbonyl-phenyl ester (0.993 g, 5.00 mmol) was added and the mixture was refluxed for 4 h. After cooling to room temperature, diethyl ether (50 mL) was added and the salts were removed by filtration. The filtrate was concentrated under reduced pressure. Additional ether (200 mL) was added and the remaining pyridine was extracted with 2N hydrochloric acid (3×30 mL). The ether was washed with brine (200 mL) and dried over anhydrous sodium sulfate. After concentration, the product was purified twice by flash chromatography on silica gel (118 g) eluting with hexanes-ethyl acetate (2:1) to give acetic acid 2-(1-methyl-2-phenethylcarbamoyl-propenylcaramoyl)-phenyl ester (0.58 g, 30%) as a yellow oil.

$^1$H NMR (CDCl$_3$): δ 12.95 (broad s, 1H), 7.82 (dd, 1H, J=7.8, 1.8), 7.48 (dt, 1H, J=7.5, 1.8), 7.31-7.12 (m, 7H), 5.71 (t, 1H, J=6.6), 3.54 (q, 2H, J=6.6), 2.82 (t, 2H, J=6.6), 2.44 (s, 3H), 2.31 (s, 3H), 1.74 (s, 3H).

$^{13}$C NMR (CDCl$_3$): δ 169.83, 169.47, 164.15, 154.31, 148.80, 146.12, 138.71, 132.00, 129.50, 128.69, 126.58, 126.22, 123.50, 105.73, 40.56, 35.49, 21.06, 17.57, 13.25.

g.) 2-(2-Hydroxy-phenyl)-5,6-dimethyl-3-phenethyl-3H-pyrimidin-4-one

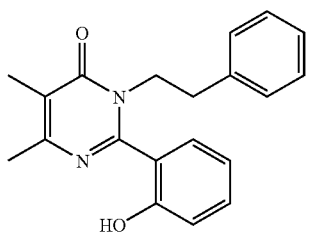

Acetic acid 2-(1-methyl-2-phenethylcarbamoyl-propenylcarbamoyl)-phenyl ester of Example 1f (220 mg, 0.59 mmol) was dissolved in the mixture of ethanol (8 mL) and water (8 mL) which contained 85% potassium hydroxide (0.80 g, 1.2 mmol). The mixture was refluxed overnight. After cooling, the reaction mixture was acidified with hydrochloric acid to pH=1 and extracted with dichloromethane (3×30 mL). The combined organic layers were washed with water (50 mL), brine (50 mL) and dried over anhydrous sodium sulfate. After concentration, the product was purified by flash chromatography on silica gel (39 g) eluting with hexanes-ethyl acetate (1:1) to give 2-(2-hydroxy-phenyl)-5,6-dimethyl-3-phenethyl-3H-pyrimidin-4-one (70 mg, 37%) as a white solid.

$^1$H NMR (CDCl$_3$): δ 7.15-7.10 (m, 4H), 7.01 (d, 1H, J=7.8), 6.82-6.78 (m, 3H), 6.71 (d, 1H, J=7.8), 4.07 (t, 1H, J=7.8), 2.80 (t, 2H, J=7.8), 2.22 (s, 3H), 2.08 (s, 3H).

$^{13}$C NMR (CDCl$_3$): δ 162.60, 157.02, 155.81, 154.24, 137.59, 131.70, 129.06, 128.64, 128.42, 126.47, 120.82, 119.77, 119.22, 117.44, 47.77, 34.26, 20.89, 11.69.

Example 5

Preparation of 3-[2-(2-Fluoro-phenyl)-ethyl]-2-(2-hydroxy-phenyl)-5,6-dimethyl-3H-pyrimidin-4-one

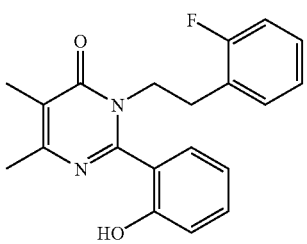

Utilizing the procedures described in Example 4a-g except substituting 2-fluoro-phenethylamine for phenethylamine in step 4c the title compound was prepared as a white solid after crystallization from hexanes-ethyl acetate (3:1).

$^1$H NMR (CDCl$_3$): δ 9.88 (broad s, 1H), 7.11 (m, 2H), 6.91-671 (m, 6H), 4.09 (t, 2H, J=7.5), 2.88 (t, 2H, J=7.5), 2.23 (s, 3H), 2.08 (s, 3H).

$^{13}$C NMR (CDCl$_3$): δ 162.69, 161.07 (d, J=243), 157.22, 155.90, 154.23, 131.53, 131.02 (d, J=4.2), 129.07, 128.34 (d, J=8.0), 124.52 (d, J=16), 124.00 (d, J=3.2), 120.77, 119.88, 119.66, 119.08, 116.99, 115.19 (d, J=22), 46.20, 27.51, 20.88, 11.51.

Example 6

Preparation of 3-[2-(3-Fluoro-phenyl)-ethyl]-2-(2-hydroxy-Phenyl)-5,6-dimethyl-3H-pyrimidin-4-one

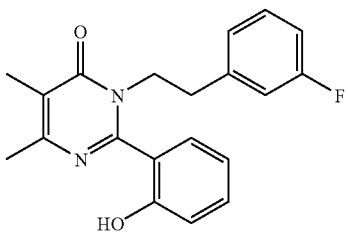

Utilizing the procedures described in Example 4a-g except substituting 3-fluoro-phenethylamine for phenethylamine in step 4c the title compound was prepared as a white solid after crystallization from hexanes-ethyl acetate (3:1).

$^1$H NMR (CDCl$_3$): δ 9.76 (broad s, 1H), 7.23 (m, 1H), 6.85 (m, 3H), 6.65 (d, 1H, J=7.8), 6.53 (m, 1H), 4.20 (t, 2H, J=7.5), 2.86 (t, 2H, J=7.5), 2.24 (s, 3H), 2.11 (s, 3H).

$^{13}$C NMR (CDCl$_3$): δ 162.73 (d, J=244), 162.63, 156.65, 155.68, 154.64, 139.98 (d, J=7.5), 132.04, 129.94 (d, J=7.4), 128.90, 124.25, 120.15, 119.88, 119.29, 118.17, 115.51 (d, J=21), 113.52 (d, J=21), 47.57, 33.99, 20.95, 11.70.

Example 7

Preparation of 3-[2-(4-Fluoro-phenyl)-ethyl]-2-(2-hydroxy-phenyl)-5,6-dimethyl-3H-pyrimidin-4-one

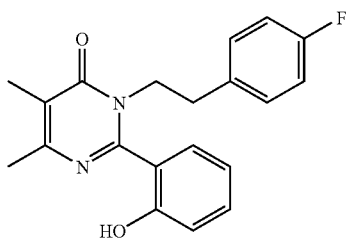

Utilizing the procedures described in Example 4a-g except substituting 4-fluoro-phenethylamine for phenethylamine in step 4c the title compound was prepared as a white solid after crystallization from hexanes-ethyl acetate (3:1).

$^1$H NMR (CDCl$_3$): δ 9.85 (broad s, 1H), 7.20 (m, 1H), 7.09 (dd, 1H, J$_1$=7.8, J$_2$=1.5), 6.81 (m, 6H), 4.13 (t, 2H, J=7.8), 2.80 (t, 2H, J=7.8), 2.23 (s, 3H), 2.10 (s, 3H).

$^{13}$C NMR (CDCl$_3$): δ 162.66, 161.66 (d, J=243), 156.69, 155.76, 154.65, 133.2 4 (d, J=3.1), 132.02, 130.09 (d, J=8.3), 128.98, 120.38, 119,92, 119.32, 118.24, 115.33 (d, J=21), 47.86, 33.50, 20.96, 11.71.

Example 8

Preparation of 5-Ethyl-2-(2-hydroxy-phenyl)-6-methyl-3-phenethyl-3H-pyrimidin-4-one

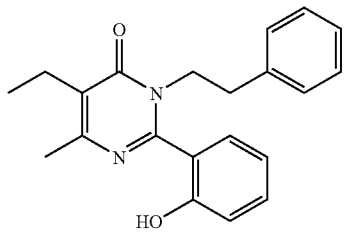

Utilizing the procedures described in Example 4a-g except substituting 2-ethyl-3-oxo-butyric acid ethyl ester for 2-methyl-3-oxo-butyric acid ethyl ester in step 4a the title compound was prepared.

$^1$H NMR (CDCl$_3$): 37.29-7.08 (m, 5H), 6.88-6.78 (m, 4H), 4.15 (t, 2H, J=7), 2.86 (t, 2H, J=7), 2.56 (q, 2H, J=7.5), 2.25 (s, 3H), 1.12 (t, 3H, J=7.5).

$^{13}$C NMR (CDCl$_3$): δ 162.60, 156.52, 156.04, 155.20, 137.89, 132.08, 129.18, 128.82, 126.78, 125.10, 119.93, 118.05, 48.12, 34.58, 20.66, 19.87, 12.60.

Example 9

Preparation of 5-Ethyl-3-[2-(2-fluoro-phenyl)-ethyl]-2-(2-hydroxy-phenyl)-6-methyl-3H-pyrimidin-4-one

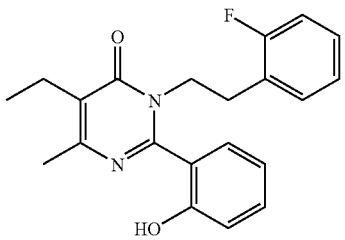

Utilizing the procedures described in Example 4a-g except substituting 2-ethyl-3-oxo-butyric acid ethyl ester for 2-methyl-3-oxo-butyric acid ethyl ester in step 4a and 2-fluoro-phenethylamine for phenethylamine in step 4c the title compound was prepared. Yield 51% after crystallization from hexanes-ethyl acetate (3:1).

$^1$H NMR (CDCl$_3$): δ 9.79 (broad s, 1H), 7.26-7.06 (m, 3H), 6.94-677 (m, 5H), 4.21 (t, 2H, J=7.2), 2.95 (t, 2H, J=7.2), 2.56 (q, 2H, J=7.6), 2.25 (s, 3H), 1.12 (t, 3H, J=7.6).

$^{13}$C NMR (CDCl$_3$): δ 162.66, 161.38 (d, J=243), 156.33, 156.12, 155.372, 132.11, 131.29 (d, J=4.6), 129.13, 128.7 (d, J=7.8), 125.06, 124.71 (d, J=16.1), 124.33 (d, J=3.4), 119.91, 118.08, 115.51 (d, J=21), 46.78, 27.94, 20.64, 19.85, 12.59.

Example 10

Preparation of 5-Ethyl-3-[2-(3-fluoro-phenyl)-ethyl]-2-(2-hydroxy-phenyl)-6-methyl-3H-pyrimidin-4-one

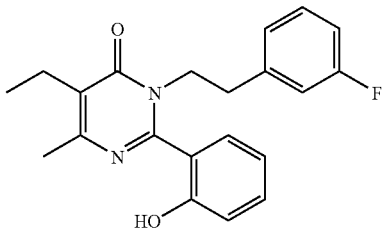

Utilizing the procedures described in Example 4a-g except substituting 2-ethyl-3-oxo-butyric acid ethyl ester for 2-methyl-3-oxo-butyric acid ethyl ester in step 4a and 3-fluoro-phenethylamine for phenethylamine in step 4c the title compound was prepared. Yield 51% after crystallization from hexanes-ethyl acetate (3:1).

$^1$H NMR (300 CDCl$_3$): δ9.66 (broad s, 1H), 7.26 (dt, 1H, J$_1$=8.0, J$_2$=1.5), 7.19-7.09 (m, 2H), 6.94-6.83 (m, 3H), 6.78 (d, 1H, J=7.7), 6.56 (dt, 1H, J$_1$=8.0, J$_2$=1.5), 4.23 (t, 2H, J=7.9), 2.89 (t, 2H, J=7.9), 2.57 (q, 2H, J=7.4), 2.27 (s, 3H), 1.14 (t, 3H, J=7.4).

$^{13}$C NMR (CDCl$_3$): δ 162.83 (d, J=244), 162.36, 157.44, 156.06, 154.35, 140.33 (d, J=7.3), 131.73, 130.01 (d, J=7.9), 124.95, 124.53, 121.24, 119.73, 116.64, 115.67 (d, J=21), 113.53 (d, J=21), 47.42, 34.07, 20.47, 19.71, 12.44.

Example 11

Preparation of 5-Ethyl-3-[2-(4-fluoro-phenyl)-ethyl]-2-(2-hydroxy-phenyl)-6-methyl-3H-pyrimidin-4-one

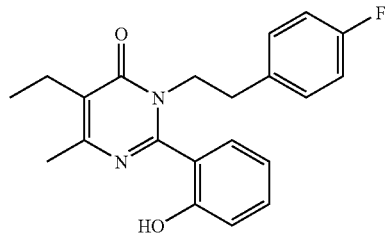

Utilizing the procedures described in Example 4a-g except substituting 2-ethyl-3-oxo-butyric acid ethyl ester for 2-methyl-3-oxo-butyric acid ethyl ester in step 4a and 4-fluorophenethylamine for phenethylamine in step 4c the title compound was prepared. Yield 51% after crystallization from hexanes-ethyl acetate (5:1).

$^1$H NMR (CDCl$_3$): δ 7.15 (dt, 1H, J$_1$=8.0, J$_2$=1.5), 7.06 (dd, 1H, J$_1$=7.8, J$_2$=1.5), 6.80-6.70 (m, 6H), 4.04 (t, 2H, J=7.5), 2.78 (t, 2H, J=7.5), 2.55 (q, 2H, J=7.5), 2.24 (s, 3H), 1.10 (t, 3H, J=7.5).

$^{13}$C NMR (CDCl$_3$): δ 162.44, 161.81 (d, J=243), 156.99, 156.08, 154.67, 133.52 (d, J=3), 131.96, 130.31 (d, J=8), 129.25, 125.07, 121.04, 119.94, 117.58, 115.45 (d, J=21), 47.81, 33.65, 20.56, 19.81, 12.54.

Example 12

Preparation of 3-[2-(3-Fluoro-phenyl)-ethyl]-2-(2-hydroxy-phenyl)-6-methyl-5-propyl-3H-pyrimidin-4-one

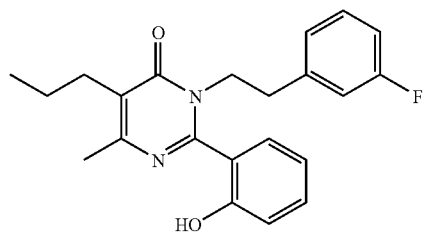

Utilizing the procedures described in Example 4a-g except substituting 2-propyl-3-oxo-butyric acid ethyl ester for 2-methyl-3-oxo-butyric acid ethyl ester in step 4a and 3-fluorophenethylamine for phenethylamine in step 4c the title compound was prepared. Yield 12% after two crystallization from hexanes-ethyl acetate (10:1).

$^1$H NMR (CDCl$_3$): δ 9.72 (broad s, 1H), 7.19-7.04 (m, 3H), 6.87-6.81 (m, 2H), 6.76 (d, 1H, J=8.2), 6.63 (dd, 1H, J=7.8), 6.50 (dt, 1H, J$_1$=8.2, J$_2$=1.8), 4.09 (t, 2H, J=7.2), 2.82 (t, 2H, J=7.2), 2.50 (t, 2H, J=8.2), 2.25 (s, 3H), 1.53 (m, 2H), 0.98 (t, 3H, J=7.2).

$^{13}$C NMR (CDCl$_3$): δ 162.95 (d, J=243), 162.67, 157.25, 156.04, 154.85, 140.28 (d, J=7.2), 132.10, 130.15 (d, J=8), 129.19, 124.57 (d, J=2.4), 123.82, 120.65, 119.95, 117.73, 115.77 (d, J=21), 113.72 (d, J=21), 47.69, 34.16, 28.55, 21.60, 20.85, 14.48.

Example 13

Preparation of 3-[2-(3-Fluoro-phenyl)-ethyl]-2-(2-hydroxy-phenyl)-5-isopropyl-6-methyl-3H-pyrimidin-4-one

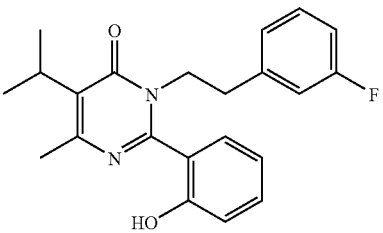

Two separate methods were utilized to prepare 3-[2-(3-Fluoro-phenyl)-ethyl]-2-(2-hydroxy-phenyl)-5-isopropyl-6-methyl-3H-pyrimidin-4-one. These two methods are identified below as Method A and Method B.

Method A: Utilizing the procedures described in Example 4a-g except substituting 2-isopropyl-3-oxo-butyric acid ethyl ester for 2-methyl-3-oxo-butyric acid ethyl ester in step 4a and 3-fluoro-phenethylamine for phenethylamine in step 4c the title compound was prepared. Yield 52% after crystallization from hexanes-ethyl acetate (10:1).

$^1$H NMR (CDCl$_3$): δ 7.21-7.09 (m, 3H), 6.85 (m, 2H), 6.76 (d, 1H, J=8.1), 6.65 (d, 1H, J=7.4), 6.52 (dd, 1H, J$_1$=8.1, J$_2$=1.5), 4.09 (t, 2H, J=7.4), 3.10 (p, 1H, J=7.0), 2.85 (t, 2H, J=7.4), 2.27 (s, 3H), 1.35 (d, 6H, J=7.0).

$^{13}$C NMR (CDCl$_3$): δ 162.95 (d, J=244), 161.70, 156.05, 155.19, 140.30 (d, J=7), 132.15, 130.16 (d, J=8), 128.98, 127.84, 124.57 (d, J=2), 120.24, 119.85, 117.91, 115.78 (d, J=21), 113.73 (d, J=21), 47.47, 34.118, 28.24, 21.41, 19.68.

Method B:

a). 3-Amino-2-isopropyl-but-3-enoic acid methyl ester

2-Methyl-3-oxo-butyric acid methyl ester (10 g, 0.0633 mol) was dissolved in absolute ethanol (50 mL). Excess of liquid ammonia (10 fold) was added and the mixture was stirred at room temperature in a sealed reaction vessel for 48 hours. Excess ammonia and ethanol were removed under reduced pressure and the crude product (73% yield according to GC-MS data) was taken as such without further purification for the next synthetic step.

b). 2-Isopropyl-3-(2-methoxy-benzoylamino)-but-3-enoic acid methyl ester

The crude 3-amino-2-isopropyl-but-3-enoic acid methyl ester of step (a) above in this method (Method B of Example 13) (5 g, 0.0318 mol) was dissolved in anhydrous THF (100 mL) and anhydrous pyridine (5.2 mL, 0.0637 mol) was added. Anisoyl chloride (4.28 mL, 0.0318 mol) was added dropwise, and the mixture was refluxed for 2 hours. After cooling, water (100 mL) was added and the organic layer was extracted with ethyl acetate (3×50 mL). The combined organic extracts were washed with 1N HCl (3×100 mL), water (100 mL), and brine (100 mL), dried over sodium sulfate and concentrated on a rotary evaporator. The product was purified by column chromatography over silica gel (200400 mesh) eluting with 10% EtOAc/hexanes to give 2-isopropyl-3-(2-methoxy-benzoylamino)but-3-enoic acid methyl ester (3 g, 33%) as a white powder.

$^1$H NMR (CDCl$_3$): δ 0.93 (d, 3H, J=6.6), 0.97 (d, 3H, J=6.6), 2.10-2.23 (m, 1H), 2.73 (d, 1H, J=11.1), 3.73 (s, 3H), 4.07 (s, 3H), 4.76 (d, 1H, J=1.2), 6.09 (s, 1H), 7.00 (d, 1H, J=8.1), 7.058-7.113 (m, 1H), 7.44-7.49 (m, 1H), 8.22 (dd, 1H, J=1.8, 6), 9.96 (br s, 1H).

$^{13}$C NMR (CDCl$_3$): δ 19.9, 21.0, 29.3, 51.9, 55.8, 60.7, 103.8, 111.4, 121.3, 121.8, 132.4, 133.0, 136.8, 157.4, 163.9, and 174.0.

c). 3-[2-(3-Fluoro-phenyl)-ethyl]-5-isopropyl-2-(2-methoxy-phenyl)-6-methyl-3H-pyrimidin-4-one Phenyl magnesium bromide (1M solution in THF, 0.0021 mol) was added to a solution of 3-fluoro-phenethyl amine (0.27 mL, 0.0021 mol) in anhydrous toluene (20 mL). After stirring the mixture at 20° C. for 10 min, 2-isopropyl-3-(2-methoxy-benzoylamino)-but-3-enoic acid methyl ester of step (b) above in this method (Method B of Example 13) (0.05 g, 0.0017 mol) was added. The mixture was refluxed for 10 hours, cooled and ethyl acetate (50 mL) was added followed by 1N HCl (50 mL). The organic layer was separated and the aqueous layer was extracted with EtOAc (3×50 mL). The combined organic extracts were washed with 1N HCl (3×100 mL), water (100 mL), and brine (100 mL). After drying over sodium sulfate and concentration on a rotatory evaporator, the product was purified by column chromatography over silica gel (200-400 mesh) eluting with 12% EtOAc/hexanes to give 3-[2-(3-fluoro-phenyl)-ethyl]-5-isopropyl-2-(2-methoxy-phenyl)-6-methyl-3H-pyrimidin-4-one (0.3 g, 46%) as a white solid.

$^1$H NMR δ 1.30 (d, 1H, J=2.7), 1.31 (d, 1H, J=2.7), 2.28 (s, 3H), 2.64-2.82 (m, 2H), 3.01-3.16 (m, 1H), 3.45-3.55 (m, 1H), 3.71 (s, 3H), 4.16-4.25 (m, 1H), 6.40 (td, 1H, J=2.4, 9.6), 6.54 (d, 1H, J=7.8), 6.87-7.08 (m, 4H), 7.35-7.41 (m, 1H).

d). 3-[2-(3-Fluoro-phenyl)-ethyl]-2-(2-hydroxy-phenyl)-5-isopropyl-6-methyl-3H-pyrimidin-4-one A dry heavy-walled Pyrex tube was charged with 3-[2-(3-fluoro-phenyl)-ethyl]-5-isopropyl-2-(2-methoxy-phenyl)-6-methyl-3H-pyrimidin-4-one of step (c) above in this method (Method B of Example 13) (50 mg, 0.000132 mole), DMSO (5 mL) and sodium cyanide (65 mg, 10 equiv). The screw cap was tightened thoroughly. The reaction mixture was exposed to microwave irradiation at 180° C. for 1 hour. The reaction mixture was allowed to reach room temperature and was carefully acidified with 50% HCl and extracted with ethyl acetate (3×25 mL). Caution, HCN may form. The combined organic extracts were washed with water (50 mL), brine (50 mL), dried over anhydrous sodium sulfate, and concentrated. The crude product, which is almost pure, was filtered through a short column packed with silica gel (200-400 mesh) using 25% EtOAc/hexanes to afford 35 mg (72%) of 3-[2-(3-fluoro-phenyl)-ethyl]-2-(2-hydroxy-phenyl)-5-isopropyl-6-methyl-3H-pyrimidin-4-one. $^1$H and $^{13}$C NMR spectral data of the compound were identical to those of the product prepared as described in Method A of Example 13.

Example 14

Preparation of 3-[2-(2-Fluoro-phenyl)-ethyl]-2-(2-hydroxy-phenyl)-5-isopropyl-6-methyl-3H-pyrimidin-one

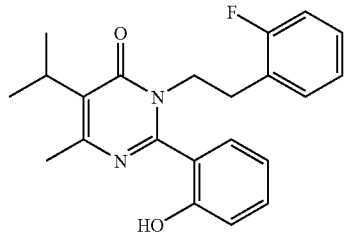

Utilizing the procedures described in Example 4a-g except substituting 2-isopropyl-3-oxo-butyric acid ethyl ester for 2-methyl-3-oxo-butyric acid ethyl ester in step 4a and 2-fluoro-phenethylamine for phenethylamine in step 4c the title compound was prepared. Yield 50% after crystallization from hexanes-ethyl acetate (10:1).

$^1$H NMR (CDCl$_3$): δ 10.10 (broad s, 1H), 7.20-7.10 (m, 2H), 7.04 (dd, 1H, J$_1$=7.7, J$_2$=1.6), 6.94-6.73 (m, 5H), 4.13 (t, 2H, J=7.0), 3.10 (m, 1H), 2.94 (t, 2H, J=7.0), 2.28 (s, 3H), 1.35 (d, 6H, J=6.9).

$^{13}$C NMR (CDCl$_3$): δ 161.81, 161.34 (d, J=244), 156.14, 155.98, 158.26, 131.92, 131.34 (d, J=4.5), 129.08, 128.65 (d, J=7.8), 127.68, 124.76 (d, J=16), 124.27 (d, J=3.3), 120.00, 119.72, 117.46, 115.45 (d, J=21.6), 46.31, 28.16, 27.85, 21.44, 19.67.

Example 15

Preparation of 2-(2-Hydroxy-phenyl)-5-methyl-3-phenethyl-6-trifluoromethyl-3H-pyrimidin-4-one

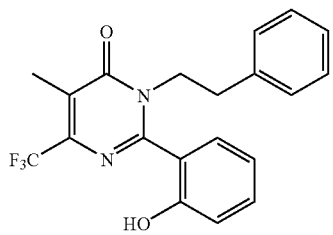

Utilizing the procedures described in Example 4a-g except substituting 2-trifluoromethyl-3-oxo-butyric acid ethyl ester for 2-methyl-3-oxo-butyric acid ethyl ester in step 4a the title compound was prepared. Yield 20% after three crystallizations from hexanes-ethyl acetate (2:1).

$^1$H NMR (CDCl$_3$) δ 10.31 (s, 1H), 7.42 (m, 1H), 7.19 (m, 3H), 7.13 (dd, 1H, J$_1$=7.6, J$_2$=1.6), 7.01 (d, 1H, J=7.9), 6.93 (m, 1H), 6.78 (m, 2H), 3.98 (t, 2H, J=7.8), 2.79 (t, 2H, J=7.8), 2.22 (q, 3H, J=2.2).

$^{13}$C NMR (CDCl$_3$): δ 162.05, 156.90, 153.88, 144.91 (q, J=32), 137.61, 131.74, 129.66, 128.57, 128.33, 126.60, 122.40, 121.76 (q, J=275), 121.40, 119.22, 115.76, 47.50, 33.17, 10.78.

Example 16

Preparation of 2-(2-Hydroxy-phenyl)-3-phenethyl-5,6,7,8-tetrahydro-3H-quinazolin-4-one

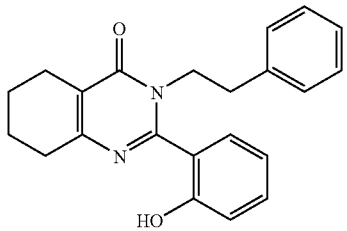

Utilizing the procedures described in Example 4a-g except substituting 2-oxo-cyclohexanecarboxylic acid ethyl ester for 2-methyl-3-oxo-butyric acid ethyl ester in step 4a the title compound was prepared. Yield 55% after crystallization from hexanes-ethyl acetate (1:1).

$^1$H NMR (CDCl$_3$): δ 10.00 (broad s, 1H), 7.14-7.00 (m, 5H), 6.80-6.69 (m, 4H), 4.02 (t, 2H, J=7.4), 2.79 (t, 2H, J=7.4), 2.5 (m, 4H), 1.68 (m, 4H).

$^{13}$C NMR (CDCl$_3$): δ 162.42, 158.75, 156.29, 154.30, 137.87, 131.77, 129.36, 128.86, 128.59, 126.63, 121.33, 120.73, 119.85, 117.18, 47.60, 34.55, 30.79, 22.62, 21.97, 21.66.

Example 17

Preparation of 3-[2-(3-Fluoro-phenyl)-ethyl]-2-(2-hydroxy-phenyl)-5,6,7,8-tetrahydro-3H-quinazolin-4-one

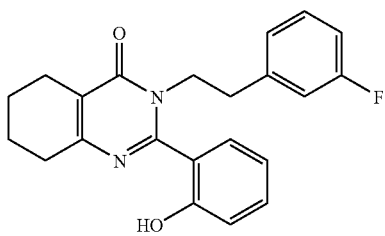

Utilizing the procedures described in Example 4a-g except substituting 2-oxo-cyclohexanecarboxylic acid ethyl ester for 2-methyl-3-oxo-butyric acid ethyl ester in step 4a and 3-fluoro-phenethylamine for phenethylamine in step 4c the title compound was prepared. Yield 56% after crystallization from hexanes-ethyl acetate (1:1).

$^1$H NMR (CDCl$_3$): δ 10.10 (broad s, 1H), 7.15-7.02 (m, 3H), 6.78-6.81 (m, 2H), 6.70 (d, 1H, J=8.1), 6.61 (d, 1H, J=7.7), 6.46 (d, 1H, J=8.1), 4.06 (t, 2H, J=7.0), 2.79 (t, 2H, J=7.0), 2.51 (m, 4H), 1.72 (m, 4H).

$^{13}$C NMR (CDCl$_3$): δ 162.92 (d, J=244), 162.42, 158.63, 156.27, 154.38, 140.30 (d, J=7.3), 132.10, 130.14 (d, J=8.3), 129.34, 124.57 (d, J=2.2), 121.18, 120.85, 120.15, 118.02, 115.76 (d, J=20.7), 113.70 (d, J=21), 47.34, 34.25, 30.83, 22.68, 22.02, 21.71.

Example 18

Preparation of 5-Cyclopropyl-3-[2-(3-fluoro-phenyl)-ethyl]-2-(2-hydroxy-phenyl)-6-methyl-3H-pyrimidin-4-one

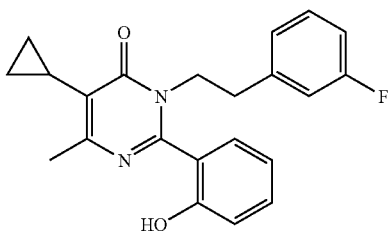

Utilizing the procedures described in Example 4a-g except substituting 2-cyclopropyl-3-oxo-butyric acid ethyl ester for 2-methyl-3-oxo-butyric acid ethyl ester in step 4a and 3-fluoro-phenethylamine for phenethylamine in step 4c the title compound was prepared. Yield 56% after crystallization from hexanes-ethyl acetate (1:1).

$^1$H NMR (CDCl$_3$): δ 9.70 (broad s, 1H), 7.31 (m, 1H), 7.15 (m, 2H), 6.91 (m, 3H), 6.70 (m, 1H), 6.59 (m, 1H), 4.25 (t, 2H, J=7.6), 2.90 (t, 2H, J=7.6), 2.38 (s, 3H), 1.61 (m, 1H), 0.99 (m, 2H), 0.87 (m, 2H).

$^{13}$C NMR (CDCl$_3$): δ 162.77 (d, J=245), 162.35, 159.27, 156.16, 154.91, 140.05 (d, J=7.3), 132.10, 129.97 (d, J=8.1), 128.83, 124.34 (d, J=2.3), 122.95, 120.02, 119.82, 118.17, 115.55 (d, J=21), 113.56 (d, J=21), 47.40, 34.03, 21.22, 8.81, 6.64.

Example 19

Preparation of 2-(2-hydroxy-phenyl)-3-phenethyl-3,5,6,7-tetrahydro-cyclopentapyrimidin-4-one Utilizing the procedures described in Example 4a-g except substituting 2-oxo-cyclopentanecarboxylic acid ethyl ester for 2-methyl-3-oxo-butyric acid ethyl ester in step 4a the title compound was prepared. Yield 52% after crystallization from hexanes-ethyl acetate (1:1).

$^1$H NMR (CDCl$_3$): δ 9.12 (broad s, 1H), 7.17 (m, 5H), 6.85 (m, 4H), 4.18 (t, 2H, J=7.8), 2.84 (m, 6H), 2.08 (m, 2H).

$^{13}$C NMR (CDCl$_3$): δ 166.59, 160.72, 158.96, 154.47, 137.61, 131.87, 128.98, 128.70, 128.51, 126.58, 123.61, 120.88, 119.86, 117.75, 47.58, 34.57, 34.33, 27.83, 21.32.

Example 20

Preparation of 3-[2-(3-fluoro-phenyl)-ethyl]-2-(2-hydroxy-phenyl)-3,5,6,7-tetrahydro-cyclopentapyrimidin-4-one

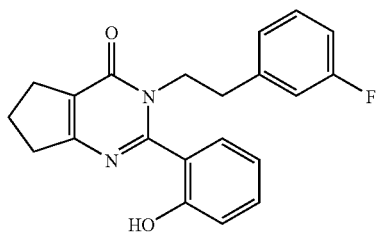

Utilizing the procedures described in Example 4a-g except substituting 2-oxo-cyclopentanecarboxylic acid ethyl ester for 2-methyl-3-oxo-butyric acid ethyl ester in step 4a and 3-fluoro-phenethylamine for phenethylamine in step 4c the title compound was prepared. Yield 51% after crystallization from hexanes-ethyl acetate (1:1).

$^1$H NMR (CDCl$_3$): δ 9.41 (broad s, 1H), 7.23 (m, 1H), 7.11 (m, 2H), 6.86 (m, 3H), 6.65 (d, 1H, J=7.6), 6.51 (d, 1H, J=9.6), 4.18 (t, 2H, J=7.7), 2.84 (m, 6H), 2.09 (m, 2H).

$^{13}$C NMR (CDCl$_3$): δ 166.95, 162.74 (d, J=245), 160.64, 159.01, 154.20, 140.07 (d, J=7.4), 131.88, 129.96 (d, J=8.1), 128.99, 124.36, 123.61, 121.10, 119.86, 117.40, 115.56 (d, J=21), 113.53 (d, J=21), 113.53 (d, J=21), 47.14, 34.29, 34.19, 27.78, 21.29.

Example 21

Preparation of 5-Ethyl-2-(2-methoxy-phenyl)-6-methyl-3-phenethyl-3H-pyrimidin-4-one To a solution of 5-ethyl-2-(2-hydroxy-phenyl)-6-methyl-3-phenethyl-3H-pyrimidin-4-one (0.19 g, 0.50 mmol) was dissolved in THF (10 mL) that contained potassium carbonate (0.80 g) and iodomethane (3 mL). The mixture was refluxed for 40 h under an argon atmosphere. After cooling to room temperature, hexanes (100 mL) were added and the salts were filtered off. The filtrate was evaporated in vacuum, and the residue was purified by flash chromatography on silica gel (40 g) eluting with ethyl acetate-hexanes (2:3) to give 5-ethyl-2-(2-methoxy-phenyl)-6-methyl-3-phenethyl-3H-pyrimidin-4-one (110 mg, 56%) as a white solid after final crystallization from hexanes.

$^1$H NMR (CDCl$_3$): δ 7.47 (d, 1H, J$_1$=7.3, J$_2$=1.8), 7.21-6.96 (m, 6H), 6.88-6.85 (m, 2H), 4.31 (m, 2H), 3.79 (s, 3H), 3.68-3.58 (m, 1H), 2.96-2.75 (m, 2H), 2.70-2.62 (m, 2H), 2.37 (s, 3H), 1.21 (t, 3H, J=7.5).

$^{13}$C NMR (CDCl$_3$): δ 162.23, 157.68, 156.01, 154.82, 138.26, 131.44, 129.75, 128.85, 128.59, 126.53, 124.83, 124.30, 121.12, 110.99, 55.56, 47.64, 34.48, 21.28, 19.82, 12.61.

Example 22

Preparation of 2-(5-Chloro-2-hydroxy-pyridin-3-yl)-5-ethyl-3-[2-(3-fluoro-phenyl)-ethyl]-6-methyl-3H-pyrimidin-4-one The title compound was prepared following the general procedures of Example 4a-g except substituting 3-fluoro-phenethylamine for phenethylamine in step 4c and 2-acetoxy-5-chloronicotinoyl chloride for acetic acid 2-chlorocarbonyl phenyl ester in step 4f.

$^1$H NMR (400 MHz, CDCl$_3$): δ 7.45 (d, J=2.8 Hz, 1H); 7.20 (m, 1H); 6.96 (m, 1H); 6.82 (d, J=2.4 Hz, 1H); 6.68 (d, J=7.6 Hz, 1H); 6.62 (ddd, J=9.6, 3.6, 2.0 Hz, 1H); 4.12 (br m, 2H); 3.01 (t, J=6.4 Hz, 2H); 2.65 (q, J=7.6 Hz, 2H); 2.34 (s, 3H); 1.21 (t, J=7.6 Hz, 3H). MS(m/z): 388.2 (M+H)$^+$.

Example 23

Preparation of 5-Ethyl-2-(3-fluoro-2-hydroxy-phenyl)-3-[2-(3-fluoro-phenyl)-ethyl]-6-methyl-3H-pyrimidin-4-one The title compound was prepared following the general procedures of Example 4a-g except substituting 3-fluoro-phenethylamine for phenethylamine in step 4c and acetic acid 2-chlorocarbonyl-6-fluoro-phenyl ester for acetic acid 2-chlorocarbonyl phenyl ester in step 4f. Yield was 65%, white solid.

$^1$H NMR (400 MHz, CDCl$_3$): δ 7.09 (m, 1H), 6.95 (m, 1H), 6.84 (m, 1H), 6.78 (ddd, J=12.8, 7.6, 4.4, 1H), 6.69 (d, J=7.7, 1H), 6.57 (d, J=7.7, 1H), 6.46 (ddd, J=9.6, 3.6, 2.0, 1H), 4.03 (t, J=7.2, 2H), 2.79 (t, J=7.6, 2H), 2.52 (q, J=7.2, 2H), 2.19 (s, 3H), 1.10 (t, J=7.2, 3H). MS (m/z): 371 (M+H)$^+$.

Example 24

Preparation of 5-Ethyl-2-(5-fluoro-2-hydroxy-phenyl)-3-[2-(3-fluoro-phenyl)-ethyl]-6-methyl-3H-pyrimidin-4-one The title compound was prepared following the general procedures of Example 4a-g except substituting 3-fluoro-phenethylamine for phenethylamine in step 4c and acetic acid 2-chlorocarbonyl-4-fluoro-phenyl ester for acetic acid 2-chlorocarbonyl phenyl ester in step 4f. Yield was 77%, white solid.

$^1$H NMR (400 MHz, CDCl$_3$): δ 7.11 (m, 1H), 6.86 (m, 2H), 6.73 (dd, J=9.2, 4.4, 1H), 6.57 (m, 2H), 6.49 (dd, J=9.6, 1.6, 1H), 4.06 (t, J=7.6, 2H), 2.83 (t, J=7.2, 2H), 2.55 (q, J=7.2, 2H), 2.24 (s, 3H), 1.11 (t, J=7.2, 3H). MS (m/z): 371 (M+H)$^+$.

Example 25

Preparation of 5-Ethyl-2-(2-fluoro-6-hydroxy-phenyl)-3-[2-(3-fluoro-phenyl)-ethyl]-6-methyl-3H-pyrimidin-4-one The title compound was prepared following the general procedures of Example 4a-g except substituting 3-fluoro-phenethylamine for phenethylamine in step 4c and acetic acid 2-chlorocarbonyl-3-fluoro-phenyl ester for acetic acid 2-chlorocarbonyl phenyl ester in step 4f. Yield was 53%, white solid.

$^1$H NMR (400 MHz, CDCl$_3$): δ 7.12 (m, 2H), 6.87 (m, 1H), 6.68 (d, J=7.6, 1H), 6.61 (m, 2H), 6.53 (ddd, J=9.6, 3.6, 2.0, 1H), 4.05 (br s, 1H), 3.95 (br s, 1H), 2.90 (br s, 1H), 2.76 (br s, 1H), 2.57 (q, J=7.2, 2H), 2.30 (s, 3H), 1.12 (t, J=7.6, 3H). MS (m/z): 371 (M+H)$^+$.

Example 26

Preparation of 2-(5-Chloro-2-hydroxy-phenyl)-5-ethyl-3-[2-(3-fluoro-phenyl)-ethyl]-6-methyl-3H-pyrimidin-4-one The title compound was prepared following the general procedures of Example 4a-g except substituting 3-fluorophenethylamine for phenethylamine in step 4c and acetic acid 4-chloro-2-chlorocarbonyl-phenyl ester for acetic acid 2-chlorocarbonyl phenyl ester in step 4f. Yield was 79%, white solid.

$^1$H NMR (400 MHz, CDCl$_3$): δ 7.15 (m, 2H), 6.91 (ddd, J=10.8, 8.0, 1.6, 1H), 6.79 (d, J=2.4, 1H), 6.70 (d, J=8.8, 1H), 6.62 (d, J=7.6, 1H), 6.53 (ddd, J=9.6, 3.6, 2.0, 1H), 4.07 (t, J=7.6, 2H), 2.89 (t, J=7.2, 2H), 2.57 (q, J=7.6, 2H), 2.26 (s, 3H), 1.14 (t, J=7.6, 3H). MS (m/z): 387 (M+H)$^+$.

Example 27

Preparation of 2-(5-Bromo-2-hydroxy-phenyl)-5-ethyl-3-[2-(3-fluoro-phenyl)-ethyl]-6-methyl-3H-pyrimidin-4-one The title compound was prepared following the general procedures of Example 4a-g except substituting 3-fluorophenethylamine for phenethylamine in step 4c and acetic acid 4-bromo-2-chlorocarbonyl-phenyl ester for acetic acid 2-chlorocarbonyl phenyl ester in step 4f. Yield was 68%, white solid.

$^1$H NMR (400 MHz, CDCl$_3$): δ 7.27 (m, 1H), 7.16 (m, 1H), 6.94 (m, 2H), 6.64 (m, 2H); 6.54 (d, J=9.6, 1H), 4.05 (t, J=7.2, 2H), 2.89 (t, J=7.2, 2H), 2.57 (q, J=7.2, 2H), 2.26 (s, 3H), 1.13 (t, J=7.6, 3H). MS (m/z): 431/433 (M+H)$^+$.

Example 28

Preparation of 5-Ethyl-3-[2-(3-fluoro-phenyl)-ethyl]-2-(2-hydroxy-3-isopropyl-phenyl)-6-methyl-3H-pyrimidin-4-one The title compound was prepared following the general procedures of Example 4a-g except substituting 3-fluorophenethylamine for phenethylamine in step 4c and acetic acid 2-chlorocarbonyl-6-isopropyl-phenyl ester for acetic acid 2-chlorocarbonyl phenyl ester in step 4f. Yield was 56%, white solid.

$^1$H NMR (400 MHz, CDCl$_3$): δ 7.26 (dd, J=7.6, 1.6, 1H), 7.14 (ddd, J=14, 8.0, 6.0, 1H), 7.05 (dd, J=7.6, 1.6, 1H), 6.89 (m, 2H), 6.67 (d, J=7.6, 1H), 6.54 (ddd, J=9.6, 3.6, 2.0, 1H), 4.28 (t, J=7.6, 2H), 3.23 (m, 1H), 2.88 (t, J=7.2, 2H), 2.58 (q, J=7.6, 2H), 2.26 (s, 3H), 1.21 (d, J=6.8, 6H), 1.16 (t, J=7.2, 3H). MS (m/z): 395.4 (M+H)$^+$.

Example 29

Preparation of 2-(3,5-Dibromo-2-hydroxy-phenyl)-5-ethyl-3-[2-(3-fluoro-phenyl)-ethyl]-6-methyl-3H-pyrimidin-4-one The title compound was prepared following the general procedures of Example 4a-g except substituting 3-fluorophenethylamine for phenethylamine in step 4c and acetic acid 2,4-dibromo 6-chlorocarbonyl-6-phenyl ester for acetic acid 2-chlorocarbonyl phenyl ester in step 4f. Yield was 62.5%, white solid.

$^1$H NMR (400 MHz, CDCl$_3$): δ 7.59 (d, J=2.4, 1H), 7.14 (ddd, J=14, 8.0, 6.0, 1H), 6.91 (dd, J=8.0, 2.0, 1H), 6.72 (d, J=2.4, 1H), 6.54 (d, J=7.6, 1H), 6.49 (dd, J=9.6, 2.0, 1H), 4.00 (t, J=7.2, 2H), 2.86 (t, J=7.2, 2H), 2.53 (q, J=7.6, 2H), 2.15 (s, 3H), 1.12 (t, J=7.6, 3H). MS (m/z): 509/511/513 (M+H)$^+$.

Example 30

Preparation of 5-Ethyl-2-(3-chloro-2-hydroxy-phenyl)-3-[2-(fluoro-phenyl)-ethyl]-6-methyl-3H-pyrimidin-4-one The title compound was prepared following the general procedures of Example 4a-g except substituting 3-fluorophenethylamine for phenethylamine in step 4c and acetic acid 2-chloro 6-chlorocarbonyl-6-isopropyl-phenyl ester for acetic acid 2-chlorocarbonyl phenyl ester in step 4f. Yield was 69%, white solid.

$^1$H NMR (400 MHz, CDCl$_3$): δ 7.28 (dd, J=7.6, 1.6 Hz, 1H); 7.10 (ddd, J=14, 8.0, 6.4 Hz, 1H); 6.83 (m, 3H); 6.57 (d, J=7.6 Hz, 1H); 6.47 (dd, J=9.6, 2.0 Hz, 1H); 4.05 (t, J=7.6 Hz, 2H); 2.82 (t, J=7.6 Hz, 2H); 2.54 (q, J=7.6 Hz, 2H); 2.18 (s, 3H); 1.12 (t, J=7.6 Hz, 3H). MS(m/z): 387 (M+H)$^+$.

Example 31

Preparation of 5-Ethyl-3-[2-(3-fluoro-phenyl)-ethyl]-2-(2-hydroxy-3-methyl-phenyl)-6-methyl-3H-pyrimidin-4-one The title compound was prepared following the general procedures of Example 4a-g except substituting 3-fluorophenethylamine for phenethylamine in step 4c and acetic acid 2-chlorocarbonyl-6-methyl-phenyl ester for acetic acid 2-chlorocarbonyl phenyl ester in step 4f. Yield was 75.6%, white solid.

$^1$H NMR (400 MHz, CDCl$_3$): δ 7.13 (m, 2H); 6.94 (dd, J=8.0, 1.6 Hz, 1H); 6.84 (m, 2H); 6.65 (d, J=7.6 Hz, 1H); 6.52 (ddd, J=9.6, 3.6, 1.6 Hz, 1H); 4.22 (t, J=7.2 Hz, 2H); 2.86 (t, J=7.6 Hz, 2H); 2.57 (q, J=7.6 Hz, 2H); 2.21 (s, 3H); 2.14 (s, 3H); 1.15 (t, J=7.6 Hz, 3H). MS(m/z): 367 (M+H)$^+$.

Example 32

Preparation of 2-(4-Chloro-2-hydroxy-phenyl)-5-ethyl-3-[2-(3-fluoro-phenyl)-ethyl]-6-methyl-3H-pyrimidin-4-one The title compound was prepared following the general procedures of Example 4a-g except substituting 3-fluorophenethylamine for phenethylamine in step 4c and acetic acid 5-chloro-2-chlorocarbonyl-phenyl ester for acetic acid 2-chlorocarbonyl phenyl ester in step 4f. Yield was 61%, white solid.

$^1$H NMR (400 MHz, CDCl$_3$): δ 7.17 (m, 1H); 6.97 (d, J=8.0 Hz, 1H); 6.90 (m, 2H); 6.81 (d, J=2.0 Hz, 1H); 6.67 (d, J=7.6 Hz, 1H); 6.59 (d, J=9.6 Hz, 1H); 4.19 (t, J=7.2 Hz, 2H); 2.90 (t, J=7.2 Hz, 2H); 2.58 (q, J=7.2 Hz, 2H); 2.26 (s, 3H); 1.15 (t, J=7.2 Hz, 3H). MS(m/z): 387 (M+H)$^+$.

Example 33

Preparation 5-Ethyl-3-[2-(3-fluoro-phenyl)-ethyl]-2-(2-hydroxy-4-methoxy-phenyl)-6-methyl-3H-Pyrimidin-4-one The title compound was prepared following the general procedures of Example 4a-g except substituting 3-fluoro-phenethylamine for phenethylamine in step 4c and acetic acid 2-chlorocarbonyl-methoxy phenyl ester for acetic acid 2-chlorocarbonyl phenyl ester in step 4f. Yield was 55%, white solid.

$^1$H NMR (400 MHz, CDCl$_3$): δ 7.17 (m, 1H); 6.88 (m, 2H); 6.72 (d, J=7.64 Hz, 1H); 6.62 (d, J=8.4 Hz, 1H); 6.47 (ddd, J=7.6, 2.4, 1.2 Hz, 1H); 6.41 (d, J=1.6 Hz, 1H); 4.25 (t, J=6 Hz, 2H); 3.80 (s, 3H); 2.82 (t, J=7.2 Hz, 2H); 2.56 (q, J=7.2 Hz, 2H); 2.26 (s, 3H); 1.15 (t, J=7.2 Hz, 3H). MS(m/z): 383 (M+H)$^+$.

The biological activity of the compounds of Formula (I) are demonstrated by the following tests:

(I) Calcium Receptor Inhibitor Assay

Calcilytic activity was measured by determining the IC$_{50}$ of the test compound for blocking increases of intracellular Ca$^{2+}$ elicited by extracellular Ca$^{2+}$ in HEK 293 4.0-7 cells stably expressing the human calcium receptor. HEK 293 4.0-7 cells were constructed as described by Rogers et al., *J. Bone Miner. Res.* 10 (*Suppl.* 1), S483, (1995) (hereby incorporated by reference herein). Intracellular Ca$^{2+}$ increases were elicited by increasing extracellular Ca$^{2+}$ from 1.0 to 1.3 mM. Intracellular Ca$^{2+}$ was measured using fluo-3, a fluorescent calcium indicator (Biotium).

The procedure was as follows:

Cells were maintained in DMEM with 10% FBS and 200 μg/ml hygromycin, under 5% CO$_2$ at 37° C. At 24-hours prior to analysis, the cells were trypsinized and plated in the above medium at 120,000 cells/well in black sided, clear-bottom, collagen I coated, 96-well plates. Plates were centrifuged at 800 rpm for 2 minutes and incubated under 5% CO$_2$ at 37°0 C overnight. The medium was then aspirated and 80 μL/well of 6 μM fluo-3 in assay buffer was added to the plate. Assay buffer contains 20 mM Na-Hepes, pH 7.4, 126 mM NaCl, 5 mM KCl, 1 mM MgCl$_2$, 1 mM CaCl$_2$, 1 mg/mL D-glucose and 1 mg/mL of bovine serum albumin (BSA; fraction V, ICN).

Cell-plates containing the fluo-3 solution were incubated in the dark, at room temperature, for 60 minutes. Following incubation plates were washed once, then refilled with 160 μL/well of assay buffer. Measurements of fluorescence were performed using the FLIPR system (Molecular Devices), with a laser setting of 0.8 W and a 0.4 second CCD camera shutter speed. A two-addition protocol was used with a 40-μL addition of buffer or test compound 95 seconds before the addition of extracellular Ca$^{2+}$. The extracellular [Ca$^{2+}$] is increased from 1.0 to 1.3 mM by adding 50 μL of 2.5 mM CaCl$_2$ in assay buffer.

Calcilytic activity was determined by a compound's ability to block, in a concentration-dependent manner, increases in the concentration of intracellular Ca$^{2+}$ elicited by increases in extracellular Ca$^{2+}$. Fluorescence signals were measured as the peak height of the response and normalized to the response elicited by extracellular Ca$^{2+}$ in the absence of test compound. All compounds were tested at 8 concentrations in duplicate with the highest concentration being 30 μM.

In general, those compounds having lower IC$_{50}$ values in the Calcium Receptor Inhibitor Assay are more preferred compounds. Compounds useful in the current invention have IC$_{50}$ values below 30 μM. Variations in solubility of the compounds tested in the calcium receptor assay may provide IC$_{50}$' values which underestimate the true potencies of these analogs. Preferred compounds are those having an IC$_{50}$ of 10 μM or lower, more preferred compounds have an IC$_{50}$ of 1 μM or lower, and most preferred compounds have an IC$_{50}$ of 0.1 μM or lower.

(II) Calcium Receptor Binding Assay

HEK 293 4.0-7 cells stably transfected with the Human Parathyroid Calcium Receptor ("HuPCaR") were scaled up in T180 tissue culture flasks. Plasma membrane is obtained by polytron homogenization or glass douncing in buffer (50 mM Tris-HCl, pH 7.4, 1 mM EDTA, 3 mM MgCl$_2$) in the presence of a protease inhibitor cocktail containing 1 μM Leupeptin, 0.04 μM Pepstatin, and 1 mM PMSF. Aliquoted membrane was snap frozen and stored at −80° C. The radioligand was radiolabeled with tritium to a radiospecific activity of 44 Ci/mmole and was aliquoted and stored in liquid nitrogen for radiochemical stability.

A typical reaction mixture contains 2 nM $^3$H compound (R,R)—N-4'-methoxy-t-3-3'-methyl-1'-ethylphenyl-1-(1-naphthyl)ethylamine, or $^3$H compound (R)—N-[2-hydroxy-3-(3-chloro-2-cyanophenoxy)propyl]-1,1-dimethyl-2-(4-methoxyphenyl)ethylamine, and 4-10 μg membrane in homogenization buffer containing 0.1% gelatin and 10% ethanol, in a reaction volume of 0.5 mL. Incubation is performed in 12×75 polyethylene tubes in an ice water bath. To each tube 25 μL of test sample in 100% ethanol is added, followed by 400 μL of cold incubation buffer, and 25 μL of 40 nM $^3$H-compound in 100% ethanol for a final concentration of 2 nM. The binding reaction is initiated by the addition of 50 μL of 80-200 μg/mL HEK 293 4.0-7 membrane diluted in incubation buffer, and allowed to incubate at 4° C. for 30 min. Wash buffer is 50 mM Tris-HCl containing 0.1% PEI. Non-specific binding is determined by the addition of 100-fold excess of unlabeled homologous ligand, and is generally 20% of total binding. The binding reaction is terminated by rapid filtration onto 1% PEI pretreated GF/C filters using a Brandel Harvestor. Filters are placed in scintillation fluid and radioactivity assessed by liquid scintillation counting.

5-Ethyl-3-[2-(2-fluoro-phenyl)-ethyl]-2-(2-hydroxy-phenyl)-6-methyl-3H-pyrimidin-4-one (1 or 3 μmol/kg) or vehicle was administered by intravenous injection over about 15 seconds to normal conscious male Sprague-Dawley rats with chronic indwelling arterial and venous catheters. Arterial blood samples were collected at 30 min and immediately before, and at 1, 5, 10, and 30 min after the start of the injection for measurement of the levels of parathyroid hormone (PTH) and ionized calcium (Ca$^{2+}$) in plasma. PTH was measured using a specific rat PTH (1-84) ELISA (Immutopics, San Clemente, Calif.). Injection of compound of Example 9 induced a rapid, but transient dose-related increase in plasma PTH levels that were maximal at 1 min after the injection. Plasma PTH levels had returned to pre-dose levels by 10 min after the injection (FIG. 1). There were no consistent changes in plasma Ca$^{2+}$ levels during this experiment (not shown).

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

It will be obvious to those having skill in the art that many changes may be made to the details of the above-described embodiments without departing from the underlying principles of the invention. The scope of the present invention should, therefore, be determined only by the following claims.

The invention claimed is:

1. A compound having the chemical formula:

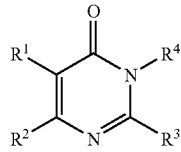

wherein:
R¹ and R² are independently H, halogen, CN, CF₃, lower alkyl, cycloalk, or aryl; or R¹ and R² are together —(CH₂)ₙ— and n is 5, 4, or 3;
R³ is aryl, which is optionally substituted by 1 to 4 substitutents on the aryl and each substitutent independently is H, halogen, CN, CF₃, OCF₃, lower alkyl, N(lower alkyl)₂, lower alkoxy, OH, OC(O)-lower alkyl, OC(O)-lower alkylamino or OC(O)-lower alkyl-N(lower alkyl)₂; and
R⁴ is —(CH₂)ₙ—R⁵ wherein n is 2, and R⁵ is aryl, which is optionally substituted by 1 to 3 substitutents on the aryl and each substitutent is independently H, halogen, lower alkyl or lower alkoxy;
or a pharmaceutically acceptable salt thereof.

2. The compound according to claim 1, wherein R¹ and R² are independently hydrogen or lower alkyl.

3. The compound according to claim 1, wherein R¹ and R² are together —(CH₂)ₙ— and n is 4 or 3.

4. The compound according to claim 2, wherein said lower alkyl is independently methyl, ethyl or isopropyl.

5. The compound according to claim 1, wherein R¹ is ethyl or isopropyl.

6. The compound according to claim 1, wherein R² is methyl.

7. The compound according to claim 3, wherein R¹ and R² together are —(CH₂)₄—.

8. The compound according to claim 1, wherein R³ is phenyl optionally substituted by hydroxy or hydroxy and fluorine.

9. The compound according to claim 1, wherein R⁵ is phenyl optionally substituted by 1 or 2 halogens.

10. The compound according to claim 9, wherein said halogens are independently fluorine or chlorine.

11. The compound according to claim 1, wherein the compound is:
2-(2-hydroxy-phenyl)-6-methyl-3-phenethyl-3H-pyrimidin-4-one;
3-[2-(2-fluoro-phenyl)-ethyl]-2-(2-hydroxy-phenyl)-6-methyl-3H-pyrimidin-4-one;
3-[2-(3-fluoro-phenyl)-ethyl]-2-(2-hydroxy-phenyl)-6-methyl-3H-pyrimidin-4-one;
2-(2-hydroxy-phenyl)-5,6-dimethyl-3-phenethyl-3H-pyrimidin-4-one;
3-[2-(2-fluoro-phenyl)-ethyl]-2-(2-hydroxy-phenyl)-5,6-dimethyl-3H-pyrimidin-4-one;
3-[2-(3-fluoro-phenyl)-ethyl]-2-(2-hydroxy-phenyl)-5,6-dimethyl-3H-pyrimidin-4-one;
3-[2-(4-fluoro-phenyl)-ethyl]-2-(2-hydroxy-phenyl)-5,6-dimethyl-3H-pyrimidin-4-one;
5-ethyl-2-(2-hydroxy-phenyl)-6-methyl-3-phenethyl-3H-pyrimidin-4-one;
5-ethyl-3-[2-(2-fluoro-phenyl)-ethyl]-2-(2-hydroxy-phenyl)-6-methyl-3H-pyrimidin-4-one;
5-ethyl-3-[2-(2-(3-fluoro-phenyl)-ethyl]-2-(2-hydroxy-phenyl)-6-methyl-3H-pyrimidin-4-one;
5-ethyl-3-[2-(4-fluoro-phenyl)ethyl]-2-(2-hydroxy-phenyl-6-methyl-3H-pyrimidin-4-one;
3-[2-(3-fluoro-phenyl)-ethyl]-2-(2-hydroxy-phenyl)-6-methyl-5-propyl-3H-pyrimidin-4-one;
3-[2-(3-fluoro-phenylyethyl]-2-(2-hydroxy-phenyl)-5-isopropyl-6-methyl-3H-pyrimidin-4-one;
3-[2-(2-fluoro-phenylyethyl]-2-(2-hydroxy-phenyl)-5-isopropyl-6-methyl-3H-pyrimidin-4-one;
2-(2-hydroxy-phenyl)-5-methyl-3-phenethyl-6-trifluoromethyl-3H-pyrimidin-4-one;
2-(2-hydroxy-phenyl)-3-phenethyl-5,6,7,8-tetrahydro-3H-quinazolin-4-one;
3[2-(3-fluoro-phenyl)ethyl]-2-(2-hydroxy-phenyl)-5,6,7,8-tetrahydro-3H-quinazolin-4-one;
5-cyclopropyl-3-[2-(3-fluoro-phenyl)-ethyl]-2-(2-hydroxy-phenyl)-6-methyl-3H-pyrimidin-4-one;
2-(2-hydroxy-phenyl)-3-phenethyl-3,5,6,7-tetrahydro-cyclopentapyrimidin-4-one;
3-[2-(3-fluoro-phenyl)-ethyl]-2-(2-hydroxy-phenyl)-3,5,6,7-tetrahydro-cyclopentapyrimidin-4-one;
5-ethyl-2-(2-methoxy-phenyl)-6-methyl-3-phenethyl-3H-pyrimidin-4-one;
3-[2-(3-fluoro-phenyl ethyl]-5-isopropyl-2-(2-methoxy-phenyl)-6-methyl-3H-pyrimidin-4-one;
2-(5-chloro-2-hydroxy-pyridin-3-yl)-5-ethyl-3-[2-(3-fluoro-phenylyethyl]-6-methyl-3H-pyrimidin-4-one;
5-ethyl-2-(3-fluoro-2-hydroxy-phenyl)-3-[2-(3-fluoro-phenyl)-ethyl]-6-methyl-3H-pyrimidin-4-one;
5-ethyl-2-(5-fluoro-2-hydroxy-phenyl)-3-[2-(3-fluoro-phenyl)ethyl]-6-methyl-3H-pyrimidin-4-one;
5-ethyl-2-(2-fluoro-6-hydroxy-phenyl)-3-[2-(3-fluoro-phenyl)-ethyl]-6-methyl-3H-pyrimidin-4-one;
2-(5-chloro-2-hydroxy-phenyl)-5-ethyl-3-[2-(3-fluoro-phenyl)-ethyl]-6-methyl-3H-pyrimidin-4-one;
2-(5-bromo-2-hydroxy-phenyl)-5-ethyl-3-[2-(3-fluoro-phenylyethyl]-6-methyl-3H-pyrimidin-4-one;
5-ethyl-3-[2-(3-fluoro-phenyl)-ethyl]-2-(2-hydroxy-3-isopropyl-phenyl)-6-methyl-3H-pyrimidin-4-one;
2-(3,5-dibromo-2-hydroxy-phenyl)-5-ethyl-3-[2-(3-fluoro-phenyl)-ethyl]-6-methyl-3H-pyrimidin-4-one;
5-ethyl-2-(3-chloro-2-hydroxy-phenyl)-3-[2-(3-fluoro-phenyl)-ethyl]-6-methyl-3H-pyrimidin-4-one;
5-ethyl-3-[2-(3-fluoro-phenyl)-ethyl]-2-(2-hydroxy-3-methyl-phenyl)-6-methyl-3H-pyrimidin-4-one;
2-(4-chloro-2-hydroxy-phenyl)-5-ethyl-3-[2-(3-fluoro-phenyl)-ethyl]-6-methyl-3H-pyrimidin-4-one; or
5-ethyl-3-[2-(3-fluoro-phenyl)-ethyl]-2-(2-hydroxy-4-methoxy-phenyl)-6-methyl-3H-pyrimidin-4-one;
or a pharmaceutically acceptable salt thereof.

12. The compound according to claim 1, wherein the compound is:
2-(2-hydroxy-phenyl)-6-methyl-3-phenethyl-3H-pyrimidin-4-one;
3-[2-(2-fluoro-phenyl)-ethyl]-2-(2-hydroxy-phenyl)-6-methyl-3H-pyrimidin-4-one;

3-[2-(3-fluoro-phenyl-ethyl]-2-(2-hydroxy-phenyl)-6-methyl-3H-pyrimidin-4-one;
2-(2-hydroxy-phenyl)-5,6-dimethyl-3-phenethyl-3H-pyrimidin-4-one;
3-[2-(2-fluoro-phenyl)ethyl]-2-(2-hydroxy-phenyl)-5,6-dimethyl-3H-pyrimidin-4-one;
3-[2-(3-fluoro-phenyl)-ethyl]-2-(2-hydroxy-phenyl)-5,6-dimethyl-3H-pyrimidin-4-one;
3-[2-(4-fluoro-phenyl)-ethyl]-2-(2-hydroxy-phenyl)-5,6-dimethyl-3H-pyrimidin-4-one;
5-ethyl-2-(2-hydroxy-phenyl)-6-methyl-3-phenethyl-3H-pyrimidin-4-one;
5-ethyl-3-[2-(2-fluoro-phenyl)-ethyl]-2-(2-hydroxy-phenyl)-6-methyl-3H-pyrimidin-4-one;
5-ethyl-3-[2-(3-fluoro-phenyl)-ethyl]-2-(2-hydroxy-phenyl)-6-methyl-3H-pyrimidin-4-one;
5-ethyl-3-[2-(4-fluoro-phenyl)-ethyl]-2-(2-hydroxy-phenyl)-6-methyl-3H-pyrimidin-4-one;
3-[2-(3-fluoro-phenylethyl]-2-(2-hydroxy-phenyl)-6-methyl-5-propyl-3H-pyrimidin-4-one;
3-[2-(3-fluoro-phenylethyl]-2-(2-hydroxy-phenyl)-5-isopropyl-6-methyl-3H-pyrimidin-4-one;
3-[2-(2-fluoro-phenyl)-ethyl]-2-(2-hydroxy-phenyl)-5-isopropyl-6-methyl-3-H-pyrimidin-4-one;
2-(2-hydroxy-phenyl)-5-methyl-3-phenethyl-6-trifluoromethyl-3H-pyrimidin-4-one;
2-(2-hydroxy-phenyl)-3-phenethyl-5,6,7,8-tetrahydro-3H-quinazolin-4-one;
3-[2-(3-fluoro-phenyl)-ethyl]-2-(2-hydroxy-phenyl)-5,6,7,8-tetrahydro-3H-quinazolin-4-one;
5-cyclopropyl-3-[2-(3-fluoro-phenyl)-ethyl]-2-(2-hydroxy-phenyl)-6-methyl-3H-pyrimidin-4-one;
2-(2-hydroxy-phenyl)-3-phenethyl-3,5,6,7-tetrahydro-cyclopentapyrimidin-4-one;
3-[2-(3-fluoro-phenylethyl]-2-(2-hydroxy-phenyl)-3,5,6,7-tetrahydro-cyclopentapyrimidin-4-one;
5-ethyl-2-(2-methoxy-phenyl)-6-methyl-3-phenethyl-3H-pyrimidin-4-one;
2-(5-chloro-2-hydroxy-pyridin-3-yl)-5-ethyl-3-[2-(3-fluoro-phenyl)ethyl]-6-methyl-3H-pyrimidin-4-one;
5-ethyl-2-(3-fluoro-2-hydroxy-phenyl)-3-[2-(3-fluoro-phenyl)-ethyl]-6-methyl-3H-pyrimidin-4-one;
5-ethyl-2-(5-fluoro-2-hydroxy-phenyl)-3-[2-(3-fluoro-phenyl)-ethyl]-6-methyl-3H-pyrimidin-4-one;
5-ethyl-2-(2-fluoro-6-hydroxy-phenyl)-3-[2-(3-fluoro-phenyl)-ethyl]-6-methyl-3H-pyrimidin-4-one;
2-(5-bromo-2-hydroxy-phenyl)-5-ethyl-3-[2-(3-fluoro-phenyl)-ethyl]-6-methyl-3H-pyrimidin-4-one;
5-ethyl-3-[2-(3-fluoro-phenyl)-ethyl]-2-(2-hydroxy-3-isopropyl-phenyl)-6-methyl-3H-pyrimidin-4-one;
2-(3,5-dibromo-2-hydroxy-phenyl)-5-ethyl-3-[2-(3-fluoro-phenyl)-ethyl]-6-methyl-3H-pyrimidin-4-one; or
2-(4-chloro-2-hydroxy-phenyl)-5-ethyl-3-[2-(3-fluoro-phenyl)-ethyl]-6-met-hyl-3H-pyrimidin-4-one;
or a pharmaceutically acceptable salt thereof.

13. The compound according to claim 1, wherein the compound is:
2-(2-hydroxy-phenyl)-6-methyl-3-phenethyl-3H-pyrimidin-4-one;
3-[2-(2-fluoro-phenyl)-ethyl]-2-(2-hydroxy-phenyl)-6-methyl-3H-pyrimidin-4-one;
3-[2-(3-fluoro-phenyl)-ethyl]-2-(2-hydroxy-phenyl)-6-methyl-3H-pyrimidin-4-one;
2-(2-hydroxy-phenyl)-5,6-dimethyl-3-phenethyl-3H-pyrimidin-4-one;
3-[2-(2-fluoro-phenyl)-ethyl]-2-(2-hydroxy-phenyl)-5,6-dimethyl-3H-pyrimidin-4-one;
3-[2-(3-fluoro-phenyl)-ethyl]-2-(2-hydroxy-phenyl)-5,6-dimethyl-3H-pyrimidin-4-one;
3-[2-(4-fluoro-phenylyethyl]-2-(2-hydroxy-phenyl)-5,6-dimethyl-3H-pyrimidin-4-one;
5-ethyl-2-(2-hydroxy-phenyl)-6-methyl-3-phenethyl-3H-pyrimidin-4-one;
5-ethyl-3-[2-(2-fluoro-phenyl)-ethyl]-2-(2-hydroxy-phenyl)-6-methyl-3H-pyrimidin-4-one;
5-ethyl-3-[2-(3-fluoro-phenylyethyl]-2-(2-hydroxy-phenyl)-6-methyl-3H-pyrimidin-4-one;
5-ethyl-3-[2-(4-fluoro-phenyl)-ethyl]-2-(2-hydroxy-phenyl)-6-methyl-3H-pyrimidin-4-one;
3-[2-(3-fluoro-phenylyethyl]-2-(2-hydroxy-phenyl)-6-methyl-5-propyl-3H-pyrimidin-4-one;
3-[2-(3-fluoro-phenyl)-ethyl]-2-(2-hydroxy-phenyl)-5-isopropyl-6-methyl-3-H-pyrimidin-4-one;
3-[2-(2-fluoro-phenyl)-ethyl]-2-(2-hydroxy-phenyl)-5-isopropyl-6-methyl-3-H-pyrimidin-4-one;
2-(2-hydroxy-phenyl)-5-methyl-3-phenethyl-6-trifluoromethyl-3H-pyrimidin-4-one;
2-(2-hydroxy-phenyl)-3-phenethyl-5,6,7,8-tetrahydro-3H-quinazolin-4-one;
3-[2-(3-fluoro-phenyl)-ethyl]-2-(2-hydroxy-phenyl)-5,6,7,8-tetrahydro-3H-quinazolin-4-one;
5-cyclopropyl-3-[2-(3-fluoro-phenyl)-ethyl]-2-(2-hydroxy-phenyl)-6-methyl-3H-pyrimidin-4-one;
2-(2-hydroxy-phenyl)-3-phenethyl-3,5,6,7-tetrahydro-cyclopentapyrimidin-4-one;
3-[2-(3-fluoro-phenyl)-ethyl]-2-(2-hydroxy-phenyl)-3,5,6,7-tetrahydro-cyclopentapyrimidin-4-one;
5-ethyl-2-(3-fluoro-2-hydroxy-phenyl)-3-[2-(3-fluoro-phenyl)-ethyl]-6-methyl-3H-pyrimidin-4-one;
5-ethyl-2-(5-fluoro-2-hydroxy-phenyl)-3-[2-(3-fluoro-phenyl)-ethyl]-6-methyl-3H-pyrimidin-4-one;
5-ethyl-2-(2-fluoro-6-hydroxy-phenyl)-3-[2-(3-fluoro-phenyl)-ethyl]-6-methyl-3H-pyrimidin-4-one; or
2-(4-chloro-2-hydroxy-phenyl)-5-ethyl-3-[2-(3-fluoro-phenyl)-ethyl]-6-methyl-3H-pyrimidin-4-one;
or a pharmaceutically acceptable salt thereof.

14. The compound according to claim 1, wherein the compound is:
2-(2-hydroxy-phenyl)-5,6-dimethyl-3-phenethyl-3H-pyrimidin-4-one;
3-[2-(2-fluoro-phenyl)-ethyl]-2-(2-hydroxy-phenyl)-5,6-dimethyl-3H-pyrimidin-4-one;
3-[2-(3-fluoro-phenyl)-ethyl]-2-(2-hydroxy-phenyl)-5,6-dimethyl-3H-pyrimidin-4-one;
3-[2-(4-fluoro-phenyl)-ethyl]-2-(2-hydroxy-phenyl)-5,6-dimethyl-3H-pyrimidin-4-one;
5-ethyl-2-(2-hydroxy-phenyl)-6-methyl-3-phenethyl-3H-pyrimidin-4-one;
5-ethyl-3-[2-(2-fluoro-phenyl)-ethyl]-2-(2-hydroxy-phenyl)-6-methyl-3H-pyrimidin-4-one;
5-ethyl-3-[2-(3-fluoro-phenyl)-ethyl]-2-(2-hydroxy-phenyl)-6-methyl-3H-pyrimidin-4-one;
5-ethyl-3-[2-(4-fluoro-phenylyethyl]-2-(2-hydroxy-phenyl)-6-methyl-3H-pyrimidin-4-one;
3-[2-(3-fluoro-phenyl)-ethyl]-2-(2-hydroxy-phenyl)-6-methyl-5-propyl-3H-pyrimidin-4-one;
3-[2-(3-fluoro-phenyl)-ethyl]-2-(2-hydroxy-phenyl)-5-isopropyl-6-methyl-3-H-pyrimidin-4-one;
3-[2-(2-fluoro-phenyl)-ethyl]-2-(2-hydroxy-phenyl)-5-isopropyl-6-methyl-3-H-pyrimidin-4-one;
2-(2-hydroxy-phenyl)-5-methyl-3-phenethyl-6-trifluoromethyl-3H-pyrimidin-4-one;

2-(2-hydroxy-phenyl)-3-phenethyl-5,6,7,8-tetrahydro-3H-quinazolin-4-one;

3-[2-(3-fluoro-phenyl)-ethyl]-2-(2-hydroxy-phenyl-5,6,7,8-tetrahydro-3H-quinazolin-4-one;

5-cyclopropyl-3-[2-(3-fluoro-phenyl)-ethyl]-2-(2-hydroxy-phenyl)-6-methyl-3H-pyrimidin-4-one;

2-(2-hydroxy-phenyl)-3-phenethyl-3,5,6,7-tetrahydro-cyclopentapyrimidin-4-one;

3-[2-(3-fluoro-phenylethyl]-2-(2-hydroxy-phenyl)-3,5,6,7-tetrahydro-cyclopentapyrimidin-4-one;

5-ethyl-2-(3-fluoro-2-hydroxy-phenyl)-3-[2-(3-fluoro-phenyl)-ethyl]-6-methyl-3H-pyrimidin-4-one;

5-ethyl-2-(5-fluoro-2-hydroxy-phenyl)-3-[2-(3-fluoro-phenyl)-ethyl]-6-methyl-3H-pyrimidin-4-one; or 5-ethyl-2-(2-fluoro-6-hydroxy-phenyl)-3-[2-(3-fluoro-phenylyethyl]-6-meth-yl-3H-pyrimidin-4-one;

or a pharmaceutically acceptable salt thereof.

15. The compound according to claim 1, wherein the compound is:

5-ethyl-3-[2-(2-fluoro-phenyl)-ethyl]-2-(2-hydroxy-phenyl)-6-meth-yl-3H-pyrimidin-4-one; or 3-[2-(3-fluoro-phenyl)-ethyl]-2-(2-hydroxy-phenyl)-6-methyl-5-isopropyl-3-H-pyrimidin-4-one;

or a pharmaceutically acceptable salt thereof.

16. A pharmaceutical composition comprising a compound according to claim 1 and a pharmaceutically acceptable diluent or excipient.

* * * * *